Figure 1:
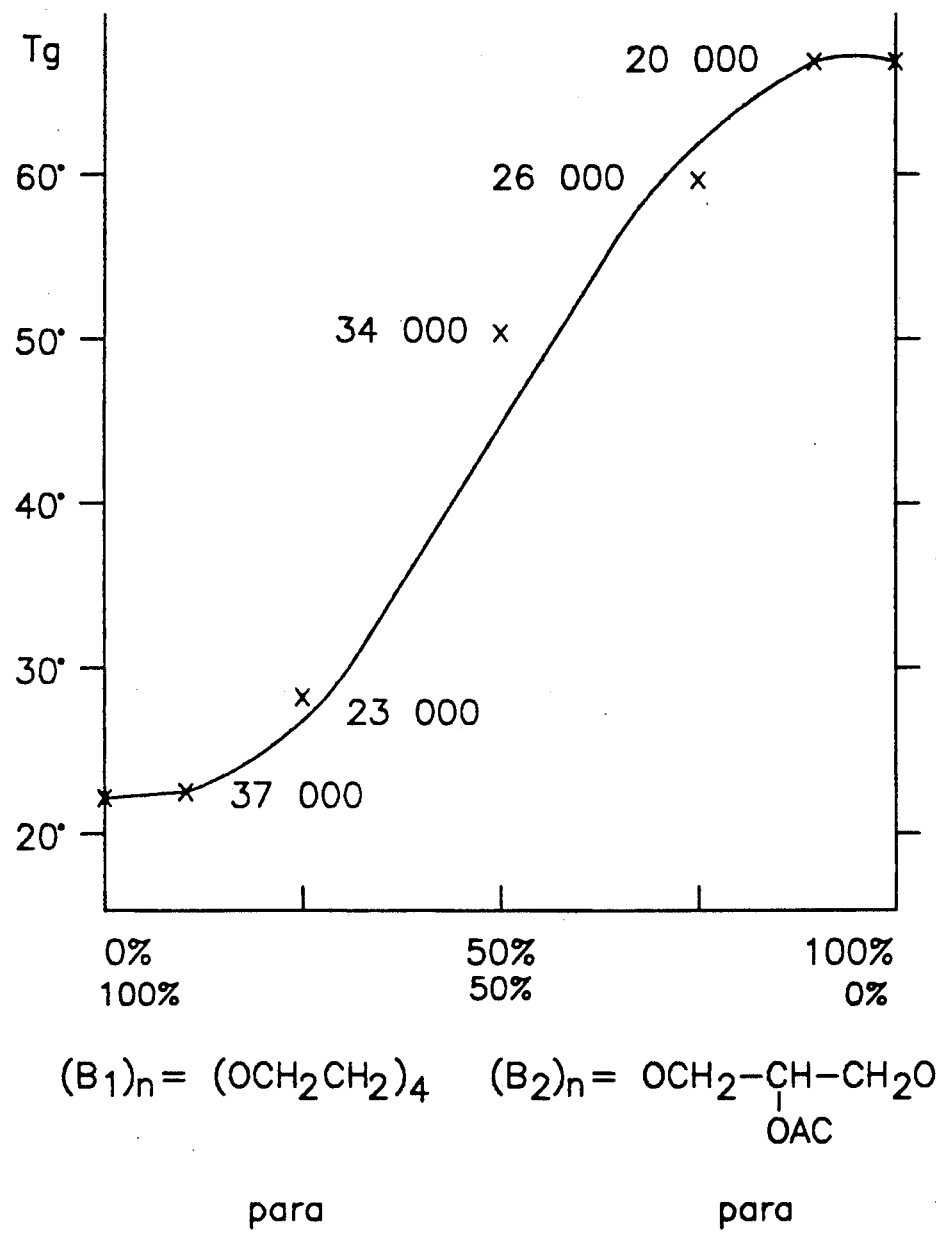

United States Patent [19]

Ziegast

[11] Patent Number: 5,091,565

[45] Date of Patent: Feb. 25, 1992

[54] POLY-DICABOXYLIC ACID ANHYDRIDES, THEIR PRODUCTION AND USE

[75] Inventor: Gerd Ziegast, Liestal, Switzerland

[73] Assignee: Sandoz Ltd., Basle, Switzerland

[21] Appl. No.: 570,939

[22] Filed: Aug. 21, 1990

Related U.S. Application Data

[60] Continuation of Ser. No. 258,305, Oct. 14, 1988, which is a division of Ser. No. 912,281, Sep. 29, 1986, Pat. No. 4,792,598.

[30] Foreign Application Priority Data

Oct. 2, 1985 [DE] Fed. Rep. of Germany ....... 3535169

[51] Int. Cl.⁵ .............................................. C07C 65/00
[52] U.S. Cl. ..................................... 562/473; 562/465; 560/255; 560/107; 260/410.5
[58] Field of Search ................ 562/473, 465; 560/107; 260/410.5

[56] References Cited

U.S. PATENT DOCUMENTS

| 4,073,935 | 2/1978 | Grill et al. ........................... 562/473 |
| 4,098,816 | 7/1978 | Thorne et al. ....................... 562/465 |
| 4,154,850 | 5/1979 | Morgan et al. ....................... 424/308 |
| 4,567,184 | 1/1986 | Musser ................................. 514/277 |

FOREIGN PATENT DOCUMENTS 5108834 8/1980 Japan .
9225142 12/1984 Japan .
2-55639 10/1990 Japan .

OTHER PUBLICATIONS

Chem. Abs. vol. 104, 1986-169167m.
Chem. Abs. vol. 103, 1985-64587z.
Chem. Abs. vol. 93, 1980-71173q.
Chem. Abs. vol. 92, 1980-110805y.
Chem. Abs. vol. 87, 1977-39235B.

*Primary Examiner*—Paul J. Killos
*Attorney, Agent, or Firm*—Gerald D. Sharkin; Robert S. Honor; Walter F. Jewell

[57] ABSTRACT

New poly-dicarboxylic acid anhydrides, which are suitable as bio-degradable matrix materials for the controlled release of medicinal agents in humans.

2 Claims, 7 Drawing Sheets $(B_1)_n = (OCH_2CH_2)_4 \quad (B_2)_n = OCH_2-\underset{OAC}{CH}-CH_2O$ para          meta

| | | |
|---|---|---|
| △ | $M_W$ 10×10³ | (3.4.4) |
| O | $M_W$ 26×10³ | (3.4.8) |
| × | $M_W$ 43×10³ | (3.4.10) |

IN VITRO

IN VITRO

IN VITRO

IN VITRO

POLY-DICABOXYLIC ACID ANHYDRIDES, THEIR PRODUCTION AND USE

This is a continuation of application Ser. No. 07/258,305, filed Oct. 14, 1988 which in turn is a division of application Ser. No. 06/912,281, filed Sept. 29, 1986, now U.S. Pat. No. 4,792,598.

The invention relates to a poly-dicarboxylic acid anhydride, its production and its use as a depot matrix material for pharmacologically active agents and as a chirurgical auxiliary material.

Poly-dicarboxylic acid anhydrides (hereinafter "polyanhydrides") are known, e.g. from Carothers and Hill in J.Am.Chem.Soc. 54 1569 and 1579 (1932) and 55 5023 (1933).

Aliphatic polyanhydrides are described, obtained from dicarboxylic acids HOOC—(CH$_2$)$_n$—COOH (n=4–16), especially sebacic acid (n=8), None of these have acquired practical significance as a result of their readiness to hydrolyse and their low melting points.

Purely aromatic polyanhydrides are also known, e.g. those consisting of terephthalic acid (PTA), described in Kunststoffe-Plastics 6, 5/1959) and Houben-Weyl 14 Vol. 2, 631, 4th edition (1963).

These polymers have remarkable stability to hydrolysis. Since they are absolutely insoluble in organic solvents, problems arise during processing to form shaped articles.

Between these two extreme cases are the polyanhydrides produced by Conix, e.g. those consisting of units of formula

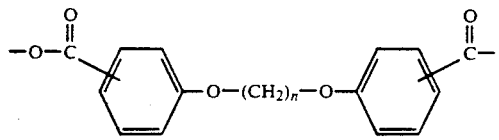

described in the British Patent 840.846, in which e.g. products with n=1 and 3 were disclosed specifically. Products having units of formula

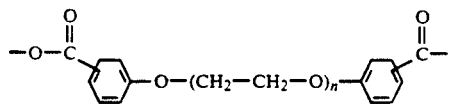

in which n=1 or 2, were also described.

All these products have greater resistance to hydrolysing reagents than the aliphatic polyanhydrides.

The products are used in the production of films, e.g. for the photography and tissues. The polyanhydrides previously mentioned all consist of units with a homo-polymeric arrangement.

Polyanhydrides consisting of units of co-polymeric arrangement are similarly known.

According to Polymer Preprints (Am.Chem.Soc.) 25, 201–202 (1984) and Biomaterials 4/2, 131–133 (1983) by Langer c.s., poly[bis(p-carboxyphenoxy)propanes (PCPP) were reacted with sebacic acid and the properties of the polymers obtained were studied.

It could be established that the hydrolysis behaviour and the melting point can be controlled by the molar ratio of the aromatic to the aliphatic component.

As well as these copolymers, homopolymers were also studied, such as a poly[bis(p-carboxyphenoxy)methane (PCPM), the PCPP already mentioned above, and a polyterephthalic acid anhydride (PTA).

It was established that compression moulded samples made of all the products studied have a very good biocompatibility after implantation in mammals. In addition, it was noticed that if the samples contained pharmacological model substances, sometimes, depending on the specific active substance - matrix system used, a significant correlation can be attained in vitro or even in vivo between matrix erosion and the release of active substance. Sometimes, significant correlation between the in vitro and the in vivo release of active substances can be observed.

The disadvantage of all the polyanhydrides previously studied is that mainly compressed articles can be made from them suitable for implants, and that no possibility exists of producing micro-capsules therefrom by spray drying or by the emulsifying process.

Solvents are needed to produce micro-capsules. However, there is a lack of suitable solvents to bring the polyanhydrides into solution.

The lack of solubility restricts the possibilities of working with these products even at the chemical production stage.

The present invention relates to a new group of polyanhydrides which can be dissolved in suitable solvents, such as CH$_2$Cl$_2$ or tetrahydrofuran, and which have good thermal and mechanical stability. Moreover there may be a linear correlation between matrix erosion and release of active substance and/or between in vitro and in vivo release of the active substance.

The present invention provides a poly-dicarboxylic acid anhydride, which contains, preferably for at least 20 mol percent, structural units of formula

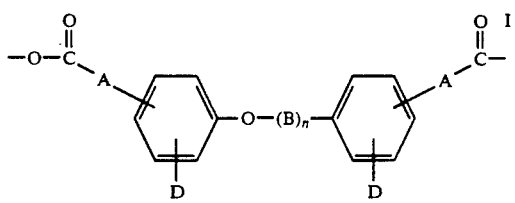

wherein

A represents a direct bond or (C$_{1-12}$)alkylene in the ortho-, meta- or para-position in the phenylring, and wherein B signifies B$_1$=—CH$_2$—CH$_2$—O— with n>2, —CH$_2$—CH$_2$—CH$_2$—O— or

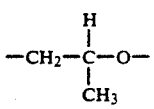

with n≧2 or

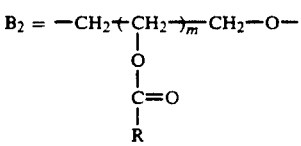

with n=1 and wherein m=1, 2, 3 or 4 and wherein R is (C$_{1-20}$)alkyl or optionally substituted phenyl or wherein

is a (co)(poly)-ester group of one or more identical or different hydroxy carboxylic acid units, and D signifies H, $CH_3$ or $OCH_3$ in ortho-, meta- or para-position on the phenyl, with a molecular weight of 2,000 to 140,000 and with the units of formula I in homo- or copolymeric arrangement, and with terminal monocarboxylic acid anhydride residues, preferably $(C_{1-13})$alkylcarboxylic acid anhydride residues, or with free carboxylic acid groups.

One homo-polymeric arrangement is one, having units of formula I in which A, B, D and n are the same.

In a copolymeric arrangement, at least one of A, B, D, n or, if $B=B_2$, m and R are different.

The invention especially provides a poly-dicarboxylic acid anhydride having a molecular weight of from 2000 to 100,000 at least 50 mol percent which consists of units of formula I in which A is a direct bond or $(C_{1-3})$alkylene, D and B in the significance of $B_1$ are as defined above and

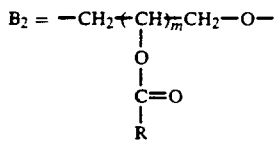

with $n=1$, and wherein $m=1$ or 3 and wherein R is $(C_{1-20})$ alkyl, or

is the group, defined as above, and having terminal $(C_{1-4})$alkylcarboxylic acid anhydride residues or free carboxylic acid groups.

Polyanhydrides in whose units A signifies $(C_{1-12})$alkylene, such as a methylene group, are for the large part insoluble in organic solvents such as $CH_2Cl_2$. Those in which A represents a direct bond are soluble on the other hand, and are therefore preferred according to the invention.

The polyanhydrides having structural units of formula I can be connected by their carbonyl groups to other units e.g. those of the known dicarboxylic acids, e.g. of the known types mentioned above such derivatives may be less soluble in organic solvents especially when intended for use as microcapsules.

Therefore the new polyanhydrides according to the invention, especially when intended for use as microcapsules, preferably consist practically completely, especially for at least 90 mol %, particularly for more than 95%, of structural units of formula I.

We have found that the glass temperature of products which consist of structural units of formula I can be influenced in particular by the position of the carbonyl group on the phenyl ring, by the identity of $B_1$ (with n) or $B_2$ (with m and R) in the molecule and by the molecular weight.

In polyanhydrides with the same molecular weight the glass temperature is reduced a) in the sequence para, meta and ortho, b) when $B=B_1$ with greater numbers of n, c) in the case of $B_2$ with greater groups R in the molecule for compounds having the same structural units the glass temperature decreases with lower molecular weights.

The glass temperature is especially important for the production of micro- capsules and may be fixed almost exactly by appropriately combining different groups $B_1$ (with n) and $B_2$ (with m and R), by varying weight ratio's within the scope of formula I and by varying molecular weight.

The invention provides in particular polyanhydrides with a copolymeric arrangement of the elements of formula I.

Thus by suitably combining the structural units of formula I, for example those in which A=direct bond, para-position, D=hydrogen

with those in which

A=direct bond, para-position, D=hydrogen

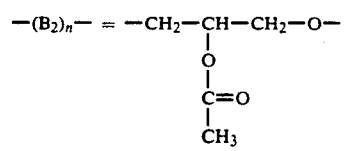

the glass temperatures are as shown graphically in FIG. 1 and by combining the structural units, for example those in which A=direct bond, para-position, D=hydrogen

with those in which

A=direct bond, meta-position, D=hydrogen

Figure 2:
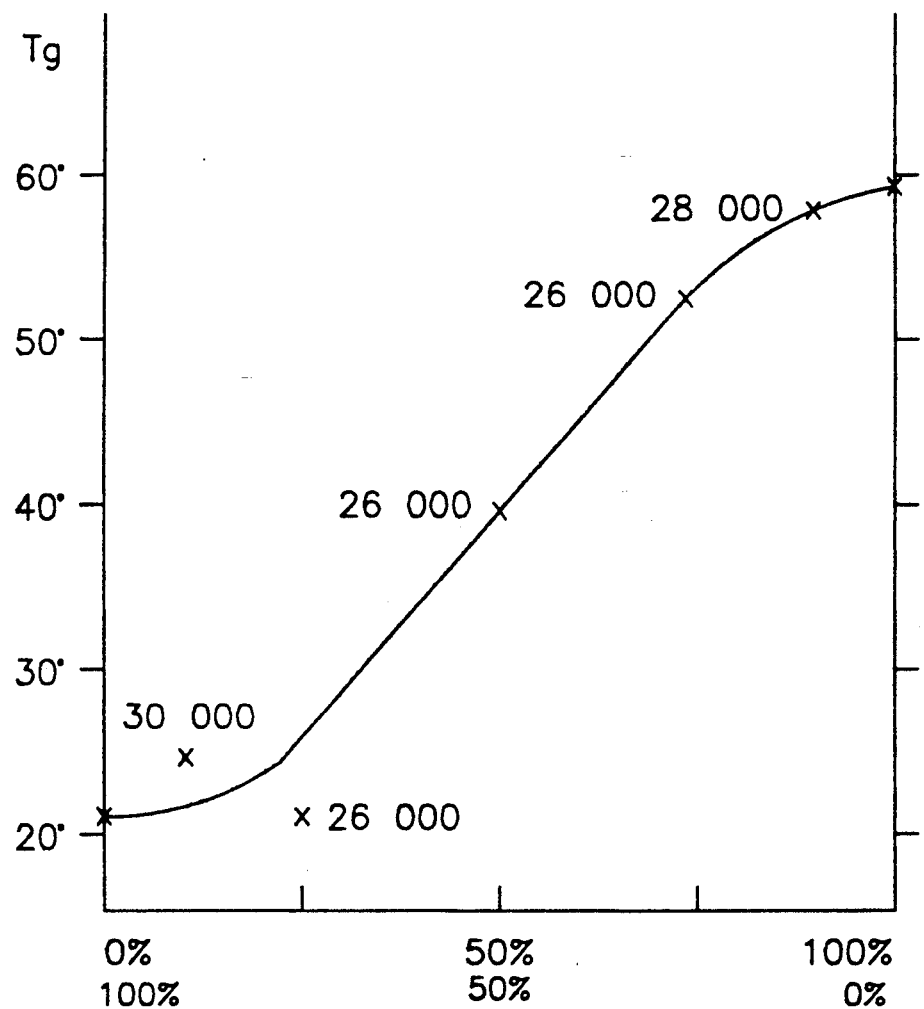

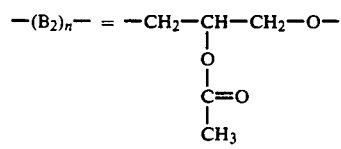

the glass temperatures are as shown in FIG. 2 (with comparable molecular weights and the same terminal acetic anhydride groups); see examples 3.22 and 3.23, which contain the basic information for FIGS. 1 and 2.

Also the hydrolysis behaviour is strongly influenced by varying the structural possibilities within the scope of the formula I and by the molecular weight.

By appropriately combining $B_1$ with $B_2$, it is possible to control the rate of hydrolysis of the molecule which is important if the polyanhydrides are used as biodegradable matrix materials for micro-capsules or implants containing pharmacologically active substances.

Groups $B_1$ have hydrophilic and groups $B_2$ hydrophobic properties and influence by their choice and by their weight proportions the rate of hydrolysis of the polymer.

As a consequence, the copolymeric polyanhydrides preferably consist of units of formula I, in which B represents a combination of $B_1$ with $B_2$.

The glass temperature and the rate of hydrolysis both depend on the same structural variation possibilities. Therefore the glass temperature gives an indication of the rate of hydrolysis.

From in vitro- and in vivo-tests, as such described in Examples 4–6, it follows that especially such polydicarboxylic acid anhydrides, having the significances of $B=B_1=-CH_2-CH_2-O-$, $n \geq 3$, $B=B_2$ with $R=(C_{1-3})$alkyl with $m=1$ in formula I and/or such having terminal $(C_{1-3})$ alkylcarboxylic acid anhydride groups, are preferred.

The polyanhydrides according to the invention can be produced by known methods, especially as follows: dicarboxylic acids, preferably at least 20 mol percent of which comprise those of formula

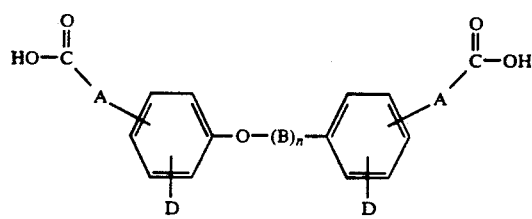

wherein

A, B, n and D possess the above-mentioned definitions, 1a) are polymerized under the influence of functional monocarboxylic acid derivatives, especially $(C_{1-13})$ alkylcarboxylic acid derivatives, to form poly-dicarboxylic acid anhydrides with terminal monocarboxylic acid anhydride residues, especially $(C_{1-13})$ alkylcarboxylic acid anhydride residues, or 1b) are polymerized with equimolar quantities of compounds of formula II in di-acid halide form, to form poly-dicarboxylic acid anhydrides with free terminal carboxylic acid groups.

The polymerisation reactions described under 1a) and 1b) are conventional e.g. from the review article in Chemisch Weekblad 63, pages 113–114 (1967). Preferably a process 1 a), with a $(C_{1-13})$alkylcarboxylic acid derivative, such as an acid halide or in particular an acid anhydride, is used, which leads to polymerisation whilst dehydrating. In this process the two carboxylic acid groups of the starting product are transformed into $(C_{1-13})$alkylcarboxylic acid anhydride groups. After polymerisation, during which a di-$(C_{1-13})$alkylcarboxylic acid anhydride is split off, the terminal groups of the end product remain however as $(C_{1-13})$alkylcarboxylic acid anhydride residues.

It is possible to use alkyl carboxylic acid derivatives having alkyl groups containing up to 13 carbon atoms. Preferably acetic acid or butyric acid derivatives are used.

A process 1 b) is also preferably used, whereby half of the quantity of the starting product is separately transformed into a di-acid halide by using an acid halide, e.g. $PCl_5$, whereafter the obtained di-acid halide is polymerised with an equimolar amount of unmodified starting product II.

The starting product II, in which B has the definition $B_1$, may be obtained in known manner, e.g. by reacting 2 mols of the compound

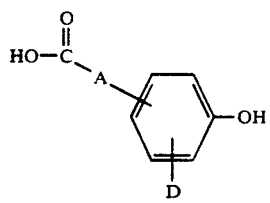

with 1 mol of the compound $Hal-(B_1)_n-Hal$, wherein Hal represents a halogen atom, especially Cl or Br. The product II, in which B has the definition $B_1$, is new and forms a part of the invention.

The reaction components are known or may be produced from known products using known processes.

The starting product II, wherein B has the definition $B_2$, especially such $B_2$, in which m is 1 or 3, can also be obtained in known manner, e.g. in such a manner that a dicarboxylic acid of formula

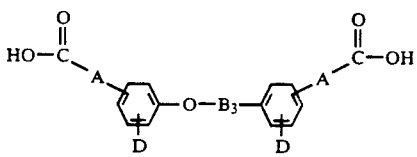

wherein

A and D are as defined above and $B_3$ is

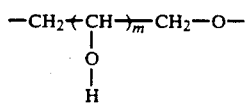

in which $m=1$, 2, 3 or 4, especially 1 or 3, 2a) is acylated on hydroxyl with functional $(C_{1-20})$alkyl- or optionally substituted phenyl-carboxylic acid derivatives, or 2b) is acylated on hydroxyl with hydroxycarboxylic acids or with their functional derivatives.

These processes are similarly effected in known manner, the process 2a) with e.g. acid halides or acid anhydrides. Mixed dicarboxylic acid anhydrides are formed, which are hydrolised subsequently, leading to the free dicarboxylic acids of formula III.

If compounds III are reacted according to process 2a) with alkylcarboxylic acid derivatives which contain a lower alkyl group, e.g. with acetic anhydride or with butyric anhydride, then both the acylation of the hydroxyl in compound III and the polymerisation and the formation of terminal alkylcarboxylic acid anhydride residues according to process 1a) can be realized in one step.

Process 2b) is preferably carried out by reacting the starting product III with lactones, e.g. dilactide, or with dilactide and additionally with lactones of other hydroxycarboxylic acids, e.g. of glycolic acid, such as diglycolide, preferably also in known manner with a catalyst, e.g. Sn octoate (see e.g. the method in U.S. Pat. No. 3.839.297).

Compound III is thereby used, in known manner, as a molecular weight regulator for the (co)(poly)ester group, by choosing its quantity in relation to the other reaction components (see e.g. the method in U.S. Pat.

Nos. 3.839.297 or 3.442.871 with glycolic acid or dodecanol as molecular weight regulators).

The starting products III can similarly be obtained in known manner, e.g. by reacting 2 mols of the compound

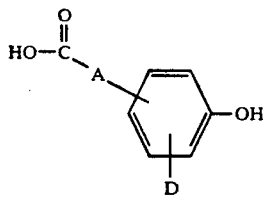

with 1 mol of the compound Hal—B$_3$—Hal

The starting products III are new and form part of the invention.

One of the possible halogen-containing products according to the formula Hal—B$_3$—Hal, (in which m=1), can be obtained in known manner, e.g. by adding a hydrohalic acid to an epihalohydrin.

The other possible halogen-containing products can be obtained in known manner e.g. by the bromination of polyols, e.g. of xylite with HBr (see e.g. Belgian Patent 876.166).

The structure of the polyanhydrides according to the invention is extremely suitable for taking up pharmacologically active subtances as a result of which a sustained release effect can be attained after injection or implantation in the body.

For the rate of release of active substance and the rate of matrix erosion, the balance between hydrophobic and hydrophilic properties plays an important role, whereby carboxycarbonyl, ethoxy and propoxy parts are hydrophilic factors and the phenyl, acyl, alkanoyl and (co) (poly)ester parts are hydrophobic factors. During their synthesis, this balance can be regulated varying the proportions of these factors, the chain length of the alkyl parts and the identity and the relative quantities of the specific hydroxycarboxylic acid units in the (co)(poly)ester part.

The degradability both of a main chain (of the anhydride units) and of side chains (the (C$_{1-20}$)alkylcarboxylic acid residues or (co)(poly) ester radicals is unexpected.

The polyanhydrides according to the invention are therefore particularly useful for the production of pharmaceutical depot forms containing pharmacologically active substances. Such depot forms may be made up of a matrix consisting of the polyanhydride which contains the active substance. Preferred depot forms are implants (e.g. for subcutaneous administration) and micro-capsules (e.g. for oral or especially for parenteral, e.g. intramuscular administration).

The object of the present invention is therefore also a pharmaceutical depot form with a matrix consisting of a product according t the invention, which contains a pharmacologically active substance.

The depot forms are new and form part of the invention.

The depot forms may be produced in known manner from the thermally and mechanically stable polyanhydrides according to the invention, and they may contain a high concentration of the active substance.

In order to produce micro-capsules, the active substance can be dissolved or suspended in a volatile solvent, such as methylene dichloride, after which a solution of the polyanhydride, e.g. in the same solvent, is added. The mixture obtained can then be sprayed into the air, during which time the temperature is carefully regulated, and then dried in the form of micro-capsules.

Another method is to dissolve or suspend the active substance in e.g. methylene dichloride, and to dissolve polyanhydride in a volatile solvent which is immiscible with water, such as methylene dichloride, after which the organic phase is mixed vigorously with a stirred aqueous solution, buffered e.g. to pH 7, which optionally contains e.g. gelatin as an emulsifier, whereafter the organic solvent is separated from the resultant emulsion and the micro-capsules formed are isolated by filtration or centrifugation. The micro-capsules are then washed (e.g. in a buffer) and dried.

In order to produce implants, the active substance can be mixed with the polyanhydride, and if the mixture is in finely-dispersed form, be pressed. If the mixture is soluble, it can be dissolved into a volatile solvent. The solvent can be evaporated and the residue ground. An extruded form can be formed from this in known manner, which yields the implant e.g. as tablets of approximately 5 to 15, e.g. 7 mm diameter and of 20–80 mg, such as 20–25 mg matrix material which is pressed e.g. at 75° C. and at 80 bar for 10 to 20 mins.

Depending on the active substance, the micro-capsules may contain up to 60% by weight thereof. Implants are preferably produced such that they contain up to 60%, e.g. 1 to 20% by weight of the active substance.

The microcapsules have a diameter of a few micrometers to a few millimeters. For pharmaceutical microcapsules, diameters of a maximum of about 250 micrometers, e.g. 10 to 60 micrometers,, are aimed at, so that they can pass easily through an injection needle.

The depot forms according to the invention can be used to as to administer very differing classes of active substances e.g. biologically active compounds, such as contraceptives, sedatives, steroids, sulphonamides, vaccines, vitamins, anti-migraine agents, proteins, peptides, enzymes, bronchodilators. cardiovascular active substances, analgesics, antibiotics, antigens, anticonvulsants, anti-inflammatory agents, anti-Parkinsons agents, prolactin secretion inhibitors, geriatrically-employable substances and anti-malaria agents.

The depot forms of the pharmaceutical compositions can be used for the known indications of the relevant active substances.

The quantities of the active substances and of the depot forms to be administered depend on various factors, e.g. the condition to be treated, the desired duration, the rate of release of the active substance and the biological degradability of the matrix.

The desired compositions can be formulated in known manner. The quantity of the required active substance and the rate of release may be determined using in vitro or in particular in vivo techniques, e.g. how long a certain concentration of active substance in the blood plasma persists at an acceptable level.

The degradability of the matrix can similarly be pursued using in vitro or in particular in vitro techniques, e.g. by weighing the quantity of matrix material which remains in the tissue after a certain period of time.

The depot forms according to the invention can be administered in the form of microcapsules e.g. subcutaneously, intramuscularly or orally, preferably as a suspension in a suitable liquid carrier or in the form of implants, e.g. subcutaneously.

For prolactin secretion inhibition with bromocryptine, for example an i.m. formulation may be produced, which daily provides 2.5 to 7.5 mg of bromocryptine over about 30 days and contains for example 70 to 230 mg bromocryptine mesylate.

The depot form can be administered again, if the plyanhydride matrix has been degraded sufficiently, e.g. after 1 to 3 months.

The poly-dicarboxylic acid anhydrides according to the invention additionally have film- and filament forming properties. The filaments have a very regularly structure, as shown from REM-measurements of in an oilbath warm stretched (T=180° C.) homo- and co-polymer dicarboxylic acid anhydrides. Other for filaments important requirements can also be met, e.g. a glass temperature between 40° and 100° C., molecular weights from 10.000 to 100.000 a high flexibility, a good elastic stretching below the glass temperature, as well as the property of obtaining a better tensile strength if the filament is cold-drawn.

The polyanhydrides can be obtained according to the melt-spinning-, the heat-spinning- and the dry-spinning process.

They possess about the same mechanical properties as the known synthetic filaments f polyamides, polyesters and polyacrylnitriles and can be used for the production of tissues.

Due to their bio-degradability the poly-di-carboxylic acid anhydrides according to the invention are suitable to be used as chirurgical sewing material or as resorbable, optionally an pharmacologically active agent containing, dressing, e.g. for internal injuries e.g. after operations.

EXAMPLE 1

Products of formula II 1.1 1,8-diphenoxy-3,6-dioxytriethane-p,p'-dicarboxylic acid

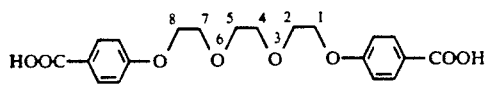

800 ml of $H_2O$, 160 g (4 mols) of NaOH (solid) and 276 g (2 mols) of p-hydroxybenzoic acid were placed in a 2.5 l flask and the solution heated to 95° C. 276 g (1 mol) of triethylene glycol dibromide were added in drops over the course of one hour, and stirred for one hour at 95° C. Then, 40 g (1 mol) of NaOH (solid) were added and stirred over 20 hours at 95° C. The reaction mixture was adjusted to pH=2-3 with 30% $H_2SO_4$, filtered whilst hot (80° C.), washed with hot water until neutral and the residue vacuum dried at 90° C.

Purification was effected by twice carrying out recrystallisation from nitrobenzene.
M.p.: 233°–235° C.
Titration: 99.4/99.7%
pKs=7.5 (DMSO/$H_2O$=75/25)

| $^1$H-NMR (360 MHz, DMSO): | |
|---|---|
| 3.6 ppm (s, 4H) | 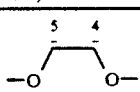 |
| 3.75 ppm (tri, 4H) | -φ-O-CH$_2$-C$\underline{H}_2$- |
| 4.15 ppm (tri, 4H) | -φ-O-C$\underline{H}_2$-CH$_2$- |
| 7.0 ppm (du, 4H$_a$) 7.9 ppm (du, 4H$_b$) | 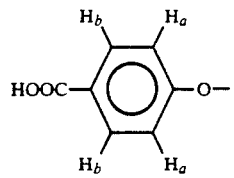 |
| 12.6 ppm (s, wide) | H$\underline{O}$OC- |

The following aromatic dicarboxylic acids (1.2–1.5) were produced analogously to example 1.1:

1.2 1,8-diphenoxy-3,6-dioxytriethane-o,o'-dicarboxylic acid
M.p.: 116°–118° C.
Titration: 99.5%
pKs=7.44 (DMSO/$H_2O$=75/25)

| $^1$H-NMR (90 MHz, DMSO): | |
|---|---|
| 3.78 ppm (s, 4H) | 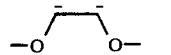 |
| 3.8–4.0 ppm (tri, 4H) | -φ-O-CH$_2$-C$\underline{H}_2$- |
| 4.3–4.4 ppm (tri, 4H) | -φ-O-C$\underline{H}_2$-CH$_2$- |
| 6.95+7.15 ppm (2×du, H$_a$) 7.05 ppm (s, H$_b$) 7.4–7.6 ppm (3×du, H$_c$) 8.0–8.15 ppm (2×du, H$_d$) | 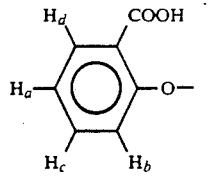 |
| ~10 ppm (s, wide) | -COO$\underline{H}$ |

1.3 1,8-diphenoxy-3,6-dioxytriethane-m,m'-dicarboxylic acid
M.p.: 180°–182° C.
Titration: 98.8/99.0%
pKs=6.9 DMSO/$H_2O$=75/25)

| $^1$H-NMR (360 MHz, DMSO): | |
|---|---|
| 3.6 ppm (s, 4H) | 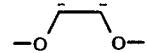 |
| 3.75 ppm (tri, 4H) | -φ-O-CH$_2$-C$\underline{H}_2$- |
| 4.15 ppm (tri, 4H) | -φ-O-C$\underline{H}_2$-CH$_2$- |
| 7.2 ppm (2×du, H$_a$) 7.4 ppm (tri, H$_b$) 7.45 ppm (s, H$_d$) 7.55 ppm (du, H$_c$) | 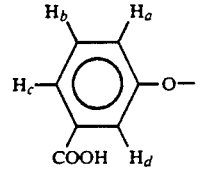 |

1.4 1,11-diphenoxy-3,6,9-trioxy-tetraethane-p,p'-dicarboxylic acid

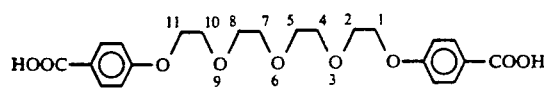

M.p.: 185°-187° C.
Titration: 99.6/100.1%
pKs=7.5 (DMSO/H₂O=75/25)

| ¹H-NMR (360 MHz, DMSO): | |
|---|---|
| 3.6 ppm (2×tri, 8H) | 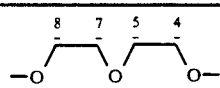 |
| 3.75 ppm (tri, 4H) | -φ-O—CH₂—C$\underline{H}_2$— |
| 4.18 ppm (tri, 4H) | -φ-O—C$\underline{H}_2$—CH₂— |
| 7.05 ppm (du, 4H$_a$) 7.9 ppm (du, 4H$_a$) | 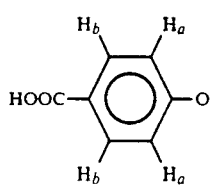 |
| 12.6 (s, wide) | $\underline{H}$OOC— |

1.5 · 1,8-diphenoxy-3,6-dioxytriethane-p,p'-diacetic acid

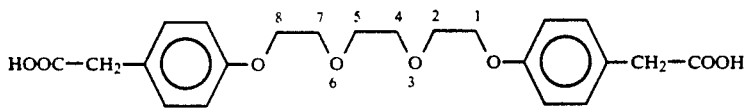

M.p.: 127°-131° C.
Titration 99.8%/100.2%  pKs=7.4 (DMSO/water=75/25)

¹H-NMR (360 MHz, DMSO) analogous to the ¹H-NMR of the compound of example 1.1 merely a new signal at δ=3.5 ppm (s,4H)

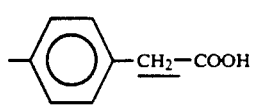

| ¹H-NMR (360 MHz, DMSO): | |
|---|---|
| 12.6 ppm (s, wide) | —COO$\underline{H}$ |

EXAMPLE 2

Products of formula III 2.1.1  1,3-diphenoxy-propan(2)ol-p,p'-dicarboxylic acid

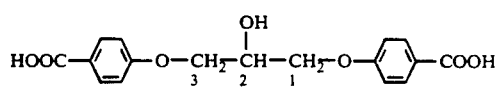

276 g (2 mols) of p-hydroxybenzoic acid, 80 g (2 mols) of NaOH (dissolved in 900 ml of H₂O) were placed in a 2.5 l flask, and 129 g (1 mol) of 1,3-dichloropropan(2)ol were added. 96 g (2.4 mols) of NaOH (dissolved in 224 ml of H₂O) were added in drops to the solution over the course of one hour, and the reaction mixture was stirred for 16 hours at 70° C., then filtered and the filtrate acidified with 15% HCl. The deposit was filtered off at 65° C. and washed with warm water (60° C.). The residue was dissolved twice in 1.5 liters of a 10% NaHCO₃ solution, heated to 50° C., and acidified (pH 1-2) with 15% HCl. The deposit was filtered off at 85° C., washed with hot water until neutral. and the raw product vacuum dried at 100° C.

For purification, 5 g of raw product were suspended twice in 100 ml of nitrobenzene, refluxed, and filtered at 180° C. The residue was washed with CH₂Cl₂ and vacuum dried at 100° C.

M.p.:~295° C. decomp.
Titration: 99.3%
pKs=7.2 DMSO/H₂O=75/25)

| ¹H-NMR (360 MHz, DMSO): | |
|---|---|
| 4.05-4.25 ppm (multi, 5H) | 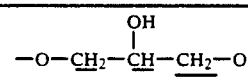 |
| 5.5 ppm (s, wide: 1H) | —O$\underline{H}$ |
| 7.05 ppm (du, 4H$_a$) 7.9 ppm (du, 4H$_b$) | 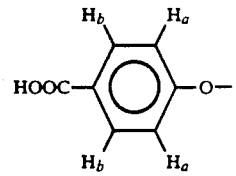 |
| ~12.6 ppm | —COO$\underline{H}$ |

The following aromatic dicarboxylic acids (2.1.2 and 2.1.3) were produced analogously to example 2.1.1:

2.1.2  1,3-diphenoxy-propan(2)ol-m,m'-dicarboxylic acid
M.p.: 192°-196° C.
Titration: 95.7% pKs=6.6 (DMSO/water=75/25)
2.1.3 1,3-diphenoxy-propan(2)ol-p,p'-diacetic acid

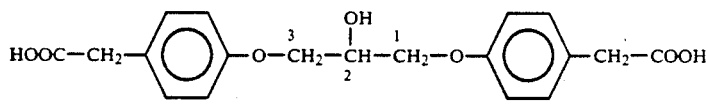

M.p.: 157.160° C.
Titration: 98.9/99.4% pKS=7.3 (DMSO/water=75/25)

¹H-NMR (90 MHz, DMSO): analogous to the ¹H-NMR of the compound 2.1.1 merely a new signal at δ=3.5 ppm (s,4H)

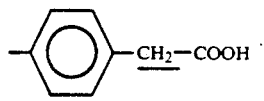

2.1.4 1,5-diphenoxy-pentane-(2,3,4)-triol-p,p'-dicarboxylic acid

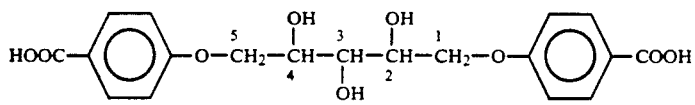

20.7 g (0.15 mole) of p-hydroxybenzoic acid were placed in a 750 ml flask and dissolved in 300 ml 1 n (0.3 mole) NaOH and heated to 75° C.

20.8 g (0.075 mole) of 1,5 dibromo-1,5-didesoxy-xylitol (prepared according to the Belgian Patent No. 876.166) were added and the mixture is stirred overnight at 75° C.

Additionally 50 ml 1 N NaOH (0.05 mole) were added and the mixture was stirred at 75° C. for 2 hours.

The reaction mixture was acidified, the formed precipitate was filtered off hot and washed with water of 80° C. The residue was purified by a two fold dissolution in NaHCO₃ solution, filtration and precipitation 5 n HCl. Finally the product was washed in ethanol and diethylether and dried in vacuo at 110° C. pKs=7.4 (DMSO/water=75/25) M.p.=274°-275° C.

| ¹H-NMR (360 MHz, DMSO) | |
|---|---|
| 3.65 ppm (tri, 1H) | —CH—CH—CH—<br>  \|   \|   \|<br>  OH  OH<br>      \|<br>      OH |
| 4.00 ppm (multi, 6H)<br>4.20 ppm | —CH₂—CH—CH—CH—CH₂—<br>    \|    \|    \|<br>    OH   OH<br>         \|<br>         OH |
| 4.85 ppm (s, wide) | —CH₂—CH—CH—CH—CH₂—<br>    \|    \|    \|<br>    OH   OH<br>         \|<br>         OH |
| 5.10 ppm (s, wide) | —CH₂—CH—CH—CH—CH₂—<br>    \|    \|    \|<br>    OH   OH<br>         \|<br>         OH |

| ¹H-NMR (360 MHz, DMSO) | |
|---|---|
| 7.00 ppm (du, 4Hₐ)<br>7.90 ppm (du, 4H_b) | 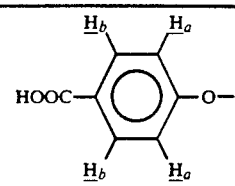 |
| 12.60 ppm (s, wide) | HOOC— |

2.2 Products of formula II, wherein B=B₂

2.2.1 1,3-diphenoxy-propan(2)oligo L(−)lactide-p,p'-dicarboxylic acid

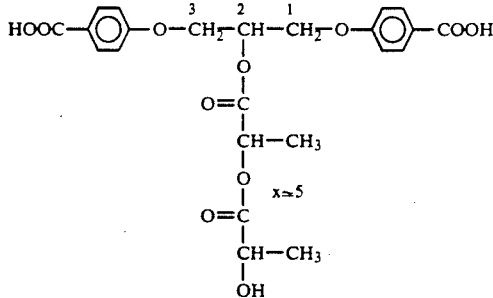

Molecular weight about 764.

1.0 g (0.003 mole) of 1.3-diphenoxy-propane-(2)-ol-p,p'-dicarboxylic acid was dissolved in 5.0 ml of pyridine and the solution was filtered.

1,3 g (0,009 mole) of L(−)-dilactide and 0,7 g of Sn (octoate)₂ were added and the reaction mixture was stirred for 10 minutes at 115° C. 10.0 ml of pyridine were added and the mixture was acidified with HCl. The reaction product was precipitated in 200 ml of water.

The aqueous solution was removed and the residue was dissolved in acetone and precipitated in 200 ml of water. The raw product was dissolved in acetone, dried over Na₂SO₄, filtered and concentrated.

| ¹H-NMR (360 MHz, DMSO): | |
|---|---|
| Backbone | |
| 4.3-4.5 ppm (multi, 4H) | 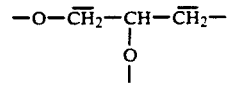 |

-continued $^1$H-NMR (360 MHz, DMSO):

| | | |
|---|---|---|
| 5.55 ppm (multi, 1H) | —O—CH$_2$—C$\underline{H}$—CH$_2$—O—<br>                        \|<br>                        O | |
| 7.05 ppm (du, 4H$_a$)<br>7.9 ppm (du, 4H$_b$) | 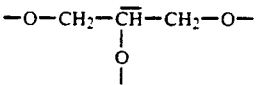 | |
| ~12.7 ppm | —COO$\underline{H}$ | |
| Side chain: | | |
| 1.2–1.3 ppm (multi, 3H) | 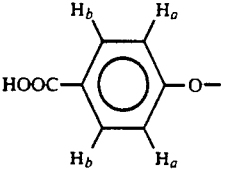 | End |
| 1.4–1.5 ppm (multi, 15H) |  | Chain |
| 4.1–4.25 ppm (multi, 1H) | 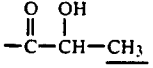 | End |
| 5.05–5.25 ppm (multi, 5H) | 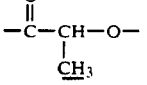 | Chain |
| 5.5 ppm (s, wide) | 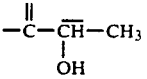 | End |

2.2.2 1,3-diphenoxy-propane—2—oligo-D,L-lactide-p,p'-dicarboxylic acid (having a structure, as indicated in Example 2.2.1, in which X≅12).

IR: Identical with that of compound 2.2.1. The signals of the ester group are more intensive.

$^1$H—NMR: Similar to that of compound 2.2.1. The intensities of the signals are stronger M$_n$≅1600.

2.2.3. 1,3-diphenoxy-propane-(-2-)-acetate-p,p'-dicarboxylic acid

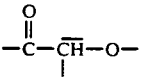

2.0 g (0.006 mole) of 1,3-diphenoxy-propane—2—ol-p,p'-dicarboxylic acid and 6.7 g (0.66 mole) of acetanhydride were heated and stirred during 30 min under reflux in a 100 ml flask.

The clear solution was diluted with 50 ml of water and stirred and heated under reflux for 3 hours.

The formed precipitate was hot filtered and washed with hot water, heated to reflux in 60 ml of water for 30 min, while stirring, hot filtered and washed with hot water. The residue was dried in vacuo at 110° C. M.p.=201°–203° C.

| $^1$H-NMR (360 MHz, DMSO) | | |
|---|---|---|
| 2.01 ppm (s, 3H) | 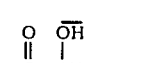 | (Side chain) |
| 4.38 ppm (tri, 4H) | —O—C$\underline{H}_2$—CH—C$\underline{H}_2$—O— | |
| 5.00 ppm (quint, 1H) | —O—CH$_2$—C$\underline{H}$—CH$_2$—O— | |
| 7.10 ppm (du, 4H$_a$)<br>7.95 ppm (du, 4H$_b$) | 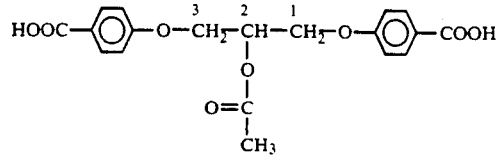 | |
| 12.60 ppm (s, 2H) | HOO$\underline{C}$— | |

2.4.4    1,3-diphenoxy-propane-(-2-)-butyrate-p,p'-dicarboxylic acid

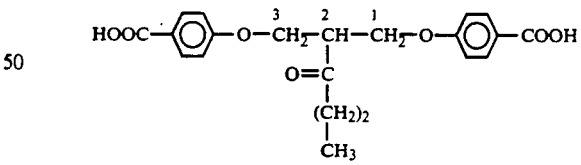

The compound was prepared analogous to compound 2.2.3

M.p. 150°–152° C.

| $^1$H-NMR | (360 MHz, DMSO) | (analogous to $^1$H-NMR of compound 2.2.3) |
|---|---|---|
| 0.86 ppm (tri, 3H) | | —O—C(=O)—CH$_2$—CH$_2$—C$\underline{H}_3$ (Side chain) |
| 1.54 ppm (quint, 2H) | | —O—C(=O)—CH$_2$—C$\underline{H}_2$—CH$_3$ (Side chain) |

| | |
|---|---|
| 2.30 ppm (tri, 2H) | 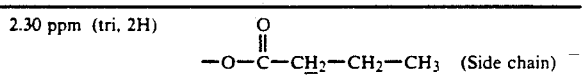 —O—C(=O)—CH₂—CH₂—CH₃ (Side chain) |
| 4.35 ppm (tri, 4H) | 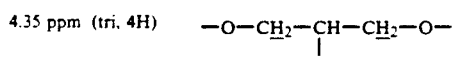 —O—CH₂—CH—CH₂—O— |
| 5.52 ppm (quint, 1H) | 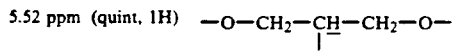 —O—CH₂—CH—CH₂—O— |

2.2.5 1,3-diphenoxy-propane—2—caprinoate-p,p'-dicarboxylic acid

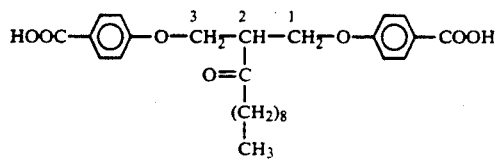

This compound was prepared from 10 g (0.03 mole) of 1,3-diphenoxy-propane-2-ol-p,p'-dicarboxylic acid, 50 ml (0.62 mole) of pyridine and 36.6 ml (0.18 mole) of capric acid chloride and was formed by hydrolysis of the reaction product.

M.p. 177°–179° C.

The solution was subsequently filtered and the filtrate concentrated under vacuum (p≦40 torr) at 80°–90° C. Polymerisation took place by raising the temperature to 230° C. (10 to 30 min) and at a vacuum of p≦0.5 torr.

The resultant product is soluble in CH₂Cl₂. The analytical characteristics are described in example 3.18. (Product No 4).

The homopolymers (soluble in CH₂Cl₂=3.2 to 3.13, poorly soluble or insoluble in CH₂Cl₂=3.14–3.17), and the copolymers (soluble in CH₂Cl₂=3.18 to 3.23, insoluble in CH₂Cl₂=3.24 and 3.25) can be produced in accordance with example 3.1.

3.2 Polymerisation product of 1,8-diphenoxy-3,6-dioxytriethane-o,o'-dicarboxylic acid with acetic anhydride ¹H-NMR (360 MHz, DMSO) (analogous to ¹H-NMR of compound 2.2.3)

| | |
|---|---|
| 0.83 ppm (tri, 3H) | 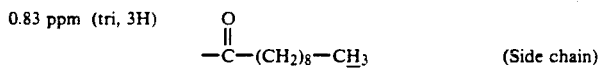 —C(=O)—(CH₂)₈—CH₃ (Side chain) |
| 1.20 ppm (s, 12H) | 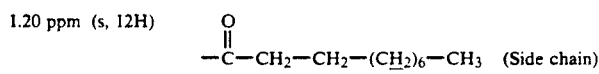 —C(=O)—CH₂—CH₂—(CH₂)₆—CH₃ (Side chain) |
| 1.50 ppm (quint, 2H) | 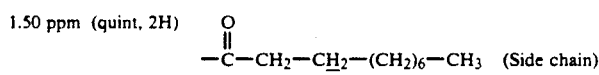 —C(=O)—CH₂—CH₂—(CH₂)₆—CH₃ (Side chain) |
| 2.30 ppm (tri, 2H) | 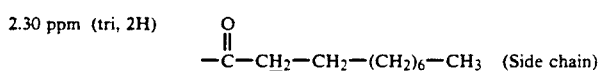 —C(=O)—CH₂—CH₂—(CH₂)₆—CH₃ (Side chain) |
| 4.35 ppm (tri, 4H) | 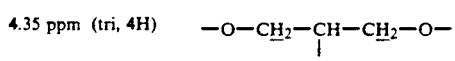 —O—CH₂—CH—CH₂—O— |
| 5.50 ppm (quint, 1H) | 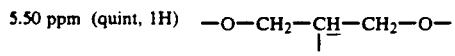 —O—CH₂—CH—CH₂—O— |

EXAMPLE 3

Products of formula I

General directions for synthesis 3.1 Copolymerisation product of 1,8-diphenoxy-3,6-dioxytriethane-p,p'-dicarboxylic acid with 1,3-diphenoxy-propan(2)-ol-p,p'-dicarboxylic acid and acetic anhydride 25 g (0.064 mole) of 1,8-diphenoxy-3,6-dioxytriethane-p,p'-dicarboxylic acid and 21.28 g (0.064 mole) of 1,3-diphenoxy-propane (2)ol-p,p'-dicarboxylic acid were dissolved in 375 ml (4 mole) of acetanhydride (p.a.) under an argon atmosphere, in a 500 ml three-necked flask, and refluxed for 2 hours at 140° C.

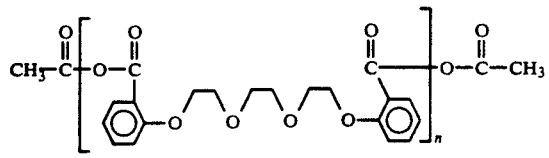

| Product No. | GPC (CH₂Cl₂/detection 250 nm) | | | DSC Tg (°C.) |
|---|---|---|---|---|
| | $M_w$ | $M_n$ | $M_w/M_n$ | |
| 1 | 13000 | 3500 | 3.7 | 6.2 |
| 2 | 23000 | 8000 | 2.9 | 13.7 |

IR(film): 1714, 1775 cm⁻¹ anhydride

¹H—NMR: as monomer 1.2, without —COOH (360 MHz, CDCl₃)

3.3 Polymerisation product of 1,8-diphenoxy-3,6-dioxytriethane-m,m'-dicarboxylic acid with acetic anhydride

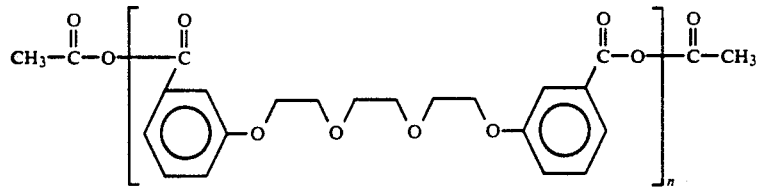

| Product No. | GPC CH₂Cl₂/detection 250 nm | | | DSC Tg (°C.) |
|---|---|---|---|---|
| | $M_w$ | $M_n$ | $M_w/M_n$ | |
| 1 | 2000 | 600 | 3.3 | |
| 2 | 16500 | 3000 | 5.5 | 19.3 |
| 3 | 25000 | 5500 | 4.5 | 20.4 |
| 4 | 52000 | 12000 | 4.3 | 21.6 |

IR(film): 1714, 1775 cm⁻¹ anhydride

¹H—NMR (360 MHz, CDCl₃) same analysis as monomer 1.3, but slight displacement of the signals (δ±0.2 ppm); no COOH signal.

3.4 Polymerisation product of 1,8-diphenoxy-3,6-dioxytriethane-p,p'-dicarboxylic acid with acetic anhydride

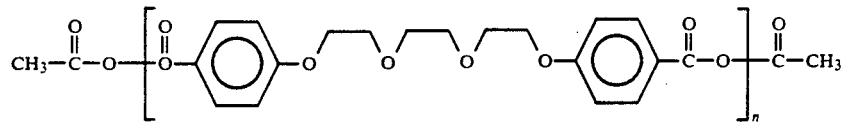

| Product No. | GPC (CH₂Cl₂/Detection 275 nm) | | | DSC Tg (°C.) |
|---|---|---|---|---|
| | $M_w$ | $M_n$ | $M_w/M_n$ | |
| 1 | 4800 | 2400 | 2.0 | −0.8 |
| 2 | 6000 | 2600 | 2.3 | |
| 3 | 8000 | 3200 | 2.5 | 13.5 |
| 4 | 10000 | 3000 | 3.3 | 26.2 |
| 5 | 12500 | 7000 | 1.8 | |
| 6 | 24000 | 10000 | 2.4 | 28.5 |
| 7 | 25000 | 7000 | 3.6 | 34.4 |
| 8 | 26500 | 8500 | 3.1 | 33.1 |
| 9 | 37000 | 13500 | 3.7 | 39.3 |
| 10 | 43500 | 14500 | 3.0 | 39.1 |
| 11 | 75500 | 32000 | 2.4 | 44.0 |
| 12 | 79000 | 20500 | 3.9 | 40.3 |
| 13 | 85000 | 26000 | 3.3 | 39.1 |
| 14 | 105000 | 13500 | 7.8 | 40.9 |
| 15 | 123000 | 16000 | 7.7 | 41.7 |
| 16 | 132000 | 16000 | 8.8 | 42.6 |

No. 10: IR(film): 1510, 1580, 1605 cm⁻¹ aromat; 1714, 1775 cm⁻¹ anhydride,
¹H-NMR (360 MHz, CDCl₃):

3.75 ppm (s, 4H)  —O—CH₂—CH₂—O—

3.9 ppm (tri 4H)  φ-O—CH₂—CH₂

4.2 ppm (tri, 4H)  φ-O—CH₂—CH₂—

6.95 ppm (du, 4H$_a$)
8.05 ppm (du, 4H$_b$)

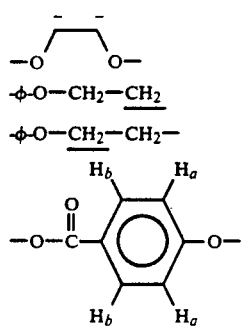

3.5 Polymerisation product of 1,11-diphenoxy-3,6,9-trioxytetraethane-p,p'-dicarboxylic acid with acetic anhydride

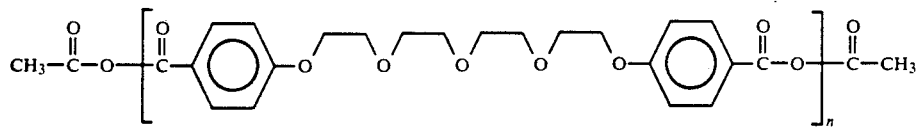

| Product No. | GPC (CH$_2$Cl$_2$/Detection 275 nm) | | | DSC Tg (°C.) |
|---|---|---|---|---|
| | M$_w$ | M$_n$ | M$_w$/M$_n$ | |
| 1 | 6250 | 1300 | 4.8 | 15.3 |
| 2 | 6500 | 2500 | 2.6 | |
| 3 | 15000 | 4000 | 3.8 | 23.5 |
| 4 | 17000 | 4000 | 4.3 | 24.3 |
| 5 | 22500 | 6500 | 3.5 | 22.2 |
| 6 | 36000 | 9500 | 3.8 | 28.1 |

No 6: $^1$H-NMR (360 MH$_z$, CDCl$_3$)

3.7 ppm (2×tri, 8H)

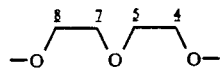

3.85 ppm (tri, 4H)

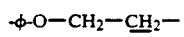

4.2 ppm (tri, 4H)

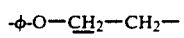

7.0 ppm (du, 4H$_a$)
8.05 ppm (du, 4H$_b$)

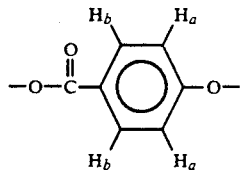

3.6 Polymerisation product of 1,3-diphenoxypropan(-2)ol-m,m'-dicarboxylic acid with acetic anhydride 3.8 Polymerisation product of 1,3-diphenoxypropan(2)ol-p,p'-dicarboxylic acid with acetic anhydride

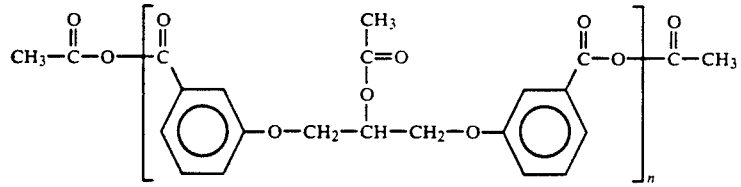

| GPC (CH$_2$Cl$_2$/detection 250 nm) | | | DSC Tg (°C.) |
|---|---|---|---|
| M$_w$ | M$_n$ | M$_w$/M$_n$ | |
| 15500 | 3500 | 4.4 | 58.3 |

3.7 Polymerisation product of 1,3-diphenoxypropan(2)ol-m,m'-dicarboxylic acid with butyric anhydride

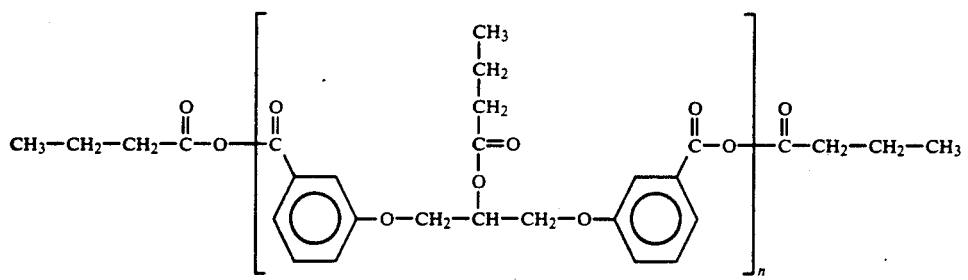

| GPC (CH$_2$Cl$_2$/detection 250 nm) | | | DSC Tg (°C.) |
|---|---|---|---|
| M$_w$ | M$_n$ | M$_w$/M$_n$ | |
| 16500 | 4500 | 3.7 | 38.8 |

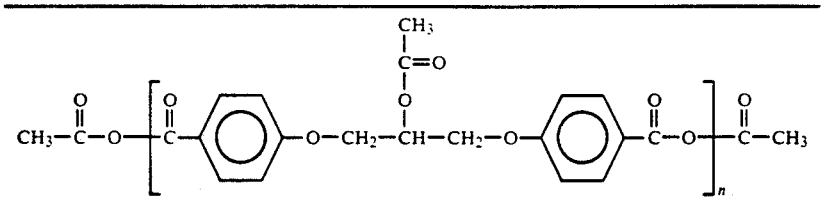

| Product | GPC (CH$_2$Cl$_2$/detection 275 nm) | | | DSC |
|---|---|---|---|---|
| No. | M$_w$ | M$_n$ | M$_w$/M$_n$ | Tg (°C.) |
| 1 | 9500 | 4000 | 2.4 | 66.7 |
| 2 | 14000 | 1500 | 9.3 | 88.8 |
| 3 | 45500 | 13000 | 3.5 | 80.7 |
| 4 | 52000 | 13000 | 4.0 | 93.0 |
| 5 | 60500 | 12000 | 5.0 | 90.5 |
| 6 | 49000 | 11800 | 4.1 | 90.4 |
| 7 | 103000 | 11000 | 9.4 | — |
| 8 | 108000 | 18000 | 6.0 | — |

No. 3: IR(film): 1510, 1582, 1605 cm$^{-1}$ aromat; 1718, 1779 cm$^{-1}$ anhydride; 1746 cm$^{-1}$ ester $^1$H-NMR (90 MHz; CDCl$_3$)
$^1$H-NMR (90 MHz; CDCl$_3$)

| | | |
|---|---|---|
| 2.15 ppm | (s, 3H) | 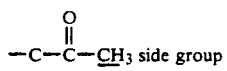 —C—C—CH$_3$ side group |
| 4.35 ppm | (du, 4H) | 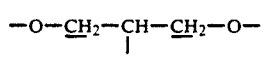 —O—CH$_2$—CH—CH$_2$—O— |
| 5.5 ppm | (quint, 1H) | 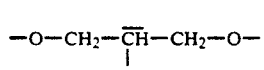 —O—CH$_2$—CH—CH$_2$—O— |
| 7.0 ppm | (du, 4H$_a$) | 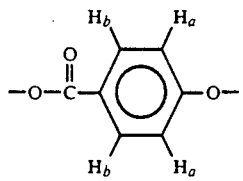 |
| 8.05 ppm | (du, 4H$_b$) | |

3.9 Polymerisation product of 1,3-diphenoxy-propan(2)ol-p,p'-dicarboxylic acid with butyric anhydride

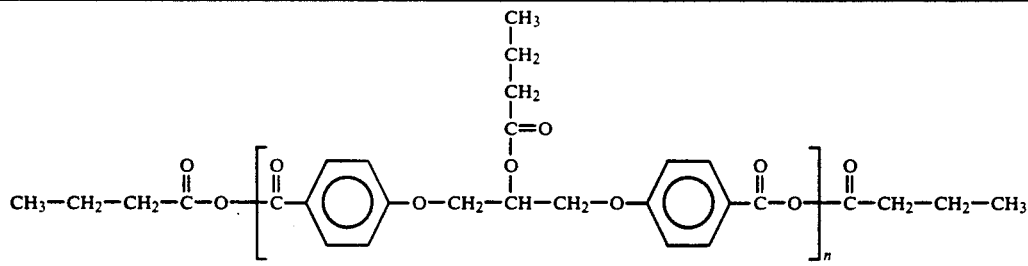

| Product | GPC (CH$_2$Cl$_2$/detection 275 nm) | | | DSC |
|---|---|---|---|---|
| No | M$_w$ | M$_n$ | M$_w$/M$_n$ | Tg (°C.) |
| 1 | 2700 | 1700 | 1.6 | 12.0 |
| 2 | 3700 | 2200 | 1.7 | 22.0 |
| 3 | 4100 | 2400 | 1.7 | 27.0 |
| 4 | 7200 | 4200 | 1.7 | 37.0 |
| 5 | 10000 | 5250 | 1.9 | 35.5 |
| 6 | 47000 | 16000 | 2.9 | 68.0 |

$^1$H-NMR (360 MHz, CDCl$_3$):
0.95 ppm (tri, 3H) 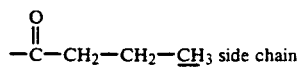 —C—CH$_2$—CH$_2$—CH$_3$ side chain

| | | |
|---|---|---|
| 1.65 ppm | (multi, 2H) | $-\overset{\overset{\text{O}}{\|}}{\text{C}}-\text{CH}_2-\underline{\text{CH}}_2-\text{CH}_3$ side chain |
| 2.35 ppm | (multi, 2H) | $-\overset{\overset{\text{O}}{\|}}{\text{C}}-\underline{\text{CH}}_2-\text{CH}_2-\text{CH}_3$ side chain |
| 4.35 ppm | (du, 4H) | $-\text{O}-\text{CH}_2-\text{CH}-\overline{\text{CH}}_2-\text{O}-$ |
| 5.55 ppm | (quad, 1H) | $-\text{O}-\text{CH}_2-\underline{\text{CH}}-\text{CH}_2-\text{O}-$ |
| 7.05 ppm<br>8.1 ppm | (du, 4H$_a$)<br>(du, 4H$_b$) | 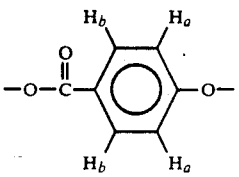 |

3.10 Polymerisation product of 1,3-diphenoxy-propane-(-2-)-caprinoate-p,p'-dicarboxylic acid with acetic acid anhydride

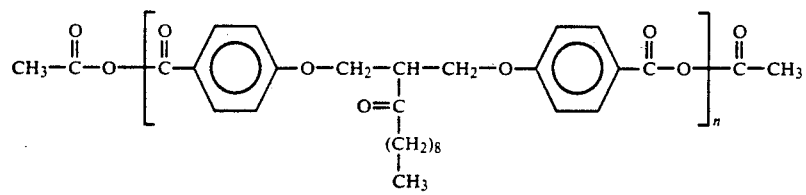

| Product | GPC (CH$_2$Cl$_2$/Detektion 275 nm) | | | DSC |
|---|---|---|---|---|
| Nr. | M$_w$ | M$_n$ | M$_w$/M$_n$ | Tg (°C.) |
| 1 | 24 000 | 7 500 | 3.2 | 34.0 |
| 2 | 31 500 | 11 000 | 2.9 | 36.9 |
| 3 | 42 500 | 11 500 | 2.7 | |
| 4 | 57 000 | 24 000 | 2.4 | |

| IR (Film): | 1510, 1582, 1605 cm$^{-1}$ | Aromatic |
| | 1718, 1780 cm$^{-1}$ | Anhydride |
| | 1741 cm$^{-1}$ | Ester |

$^1$H-NMR (360 MHz, CDCl$_3$)

| | | |
|---|---|---|
| 0.85 ppm | (tri, 3H) | $-\overset{\overset{\text{O}}{\|}}{\text{C}}-(\text{CH}_2)_8-\underline{\text{CH}}_3$ (Side chain) |
| 1.25 ppm | (s, 12H) | $-\overset{\overset{\text{O}}{\|}}{\text{C}}-\text{CH}_2-\text{CH}_2-(\underline{\text{CH}}_2)_6-\text{CH}_3$ (Side chain) |
| 1.65 ppm | (quint, 2H) | $-\overset{\overset{\text{O}}{\|}}{\text{C}}-\text{CH}_2-\underline{\text{CH}}_2-(\text{CH}_2)_6-\text{CH}_3$ (Side chain) |
| 2.40 ppm | (tri, 2H) | $-\overset{\overset{\text{O}}{\|}}{\text{C}}-\underline{\text{CH}}_2-\text{CH}_2-(\text{CH}_2)_6-\text{CH}_3$ (Side chain) |
| 4.35 ppm | (du, 4H) | $-\text{O}-\underline{\text{CH}}_2-\text{CH}-\underline{\text{CH}}_2-\text{O}-$ |
| 5.55 ppm | (quint, 1H) | $-\text{O}-\text{CH}_2-\underline{\text{CH}}-\text{CH}_2-\text{O}-$ |

| | | |
|---|---|---|
| 7.05 ppm | (du, 4H$_a$) | 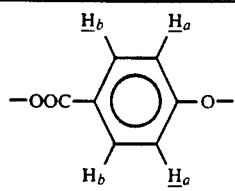 |
| 8.10 ppm | (du, 4H$_b$) | |

3.11 Polymerisation product of 1,3-diphenoxypropan(2)oligo-L(−)lactide-p,p'-dicarboxylic acid with acetic anhydride 3.12 Polymerisation product of 1,3-diphenoxypropane(2)oligo-DL-lactide-p,p'-dicarboxylic acid with acetic anhydride

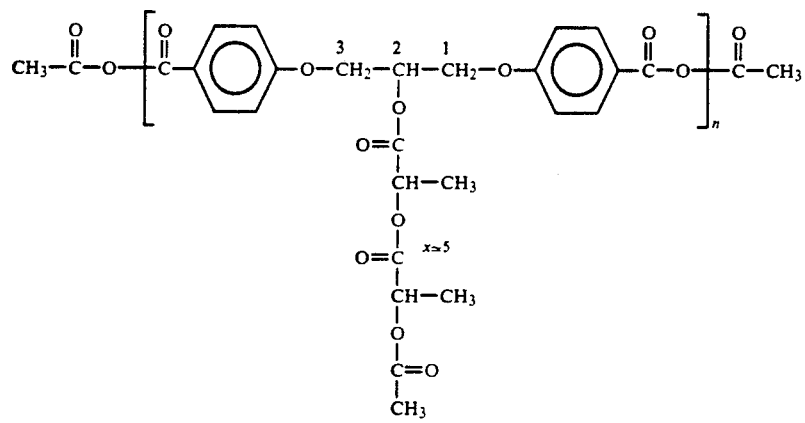

In an analogous manner products of the same formula in which x = 1 to 400 can be prepared.

| GPC (CH$_2$Cl$_2$/detection 275 nm) | | | DSC |
|---|---|---|---|
| M$_w$ | M$_n$ | M$_w$/M$_n$ | Tg (°C.) |
| 11.500 | 2 000 | 5.8 | 59.4 |

IR (film): 1512, 1582, 1606 cm$^{-1}$ aromatic; 1720, 1757 (shoulder) cm$^{-1}$ anhydride; 1757 cm$^{-1}$ ester; 2945, 2970, 2994 cm$^{-1}$ CH$_3$, CH$_2$, CH $^1$H-NMR (360 MHz, CDCl$_3$):

| | | | |
|---|---|---|---|
| Backbone | 4.35 ppm | (du, 4H) | 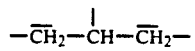 |
| | 5.6 ppm | (quint, 1H) | 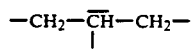 |
| | 7.0 ppm | (du, 4H$_a$) | 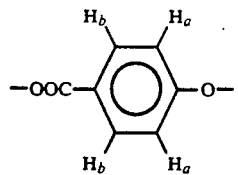 |
| | 8.1 ppm | (du, 4H$_b$) | |
| Side chain | 1.5–1.6 ppm | (multi, 18 H) | 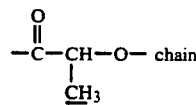 |
| | 2.1 ppm | (s, 3H) | 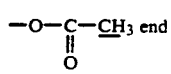 |
| | 5.05–5.2 | (multi, 6H) | 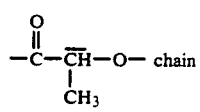 |

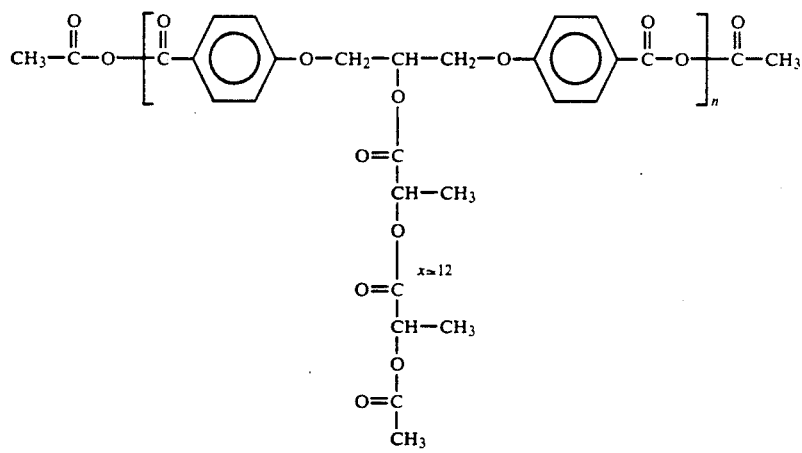

Products of the same formula in which x = 1 to 400 are obtained similarly.

| GPC (CH$_2$Cl$_2$/Detection 275 nm) | | | DSC |
|---|---|---|---|
| M$_w$ | M$_n$ | M$_w$/M$_n$ | Tg (°C.) |
| 43 000 | 18 000 | 2.4 | 52.9 |

IR: identical with 3.11. Signals for the ester groups are more intense $^1$H—NMR: Similar to 3.11, intensities of the signals of the side groups are greater.

3.13 Polymerisation product of 1.5-diphenoxy-pentane-(2,3,4)-triol-p,p'-dicarboxylic acid with butyric acid anhydride

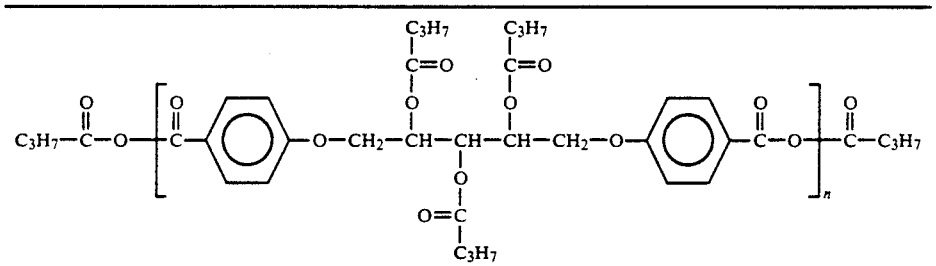

| | GPC (CH$_2$CL$_2$/Detection 275 nm) | | | |
|---|---|---|---|---|
| Product Nr. | M$_w$ | M$_n$ | M$_w$/M$_n$ | DSC Tg (°C.) |
| 1 | 40000 | 12500 | 3.2 | 52.6 |
| 2 | 39000 | 9500 | 4.1 | |

$^1$H-NMR (360 MHz/CDCl$_3$)

0.95 ppm (tri, 9H 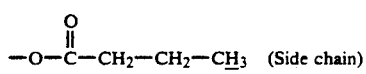 (Side chain)

1.65 ppm (multi, 6H) 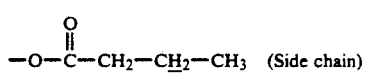 (Side chain)

2.35 ppm (multi, 6H)  (Side chain)

4.22 ppm (multi, 4H) 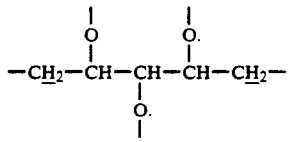

| | |
|---|---|
| 5.50 ppm (quad, 2H) | 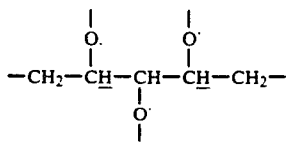 |
| 5.80 ppm (tri, 1H) | 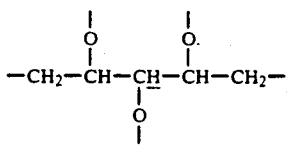 |
| 6.95 ppm (du, 4H$_a$)<br>8.05 ppm (du, 4H$_b$) | 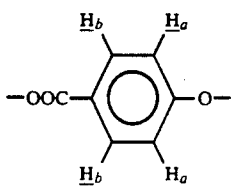 |
3.14 Polymerisation product of 1.5-Diphenoxy-pentane-(2,3,4)-triol-p,p'-dicarboxylic acid with acetic acid anhydride
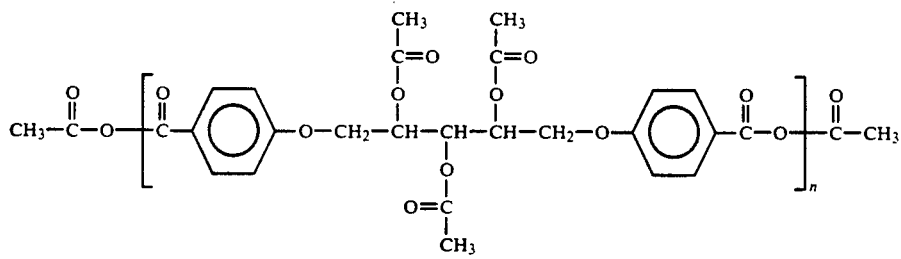
| GPC (THF/Detection 275 nm) | | | |
|---|---|---|---|
| M$_w$ | M$_n$ | M$_w$/M$_n$ | DSC Tg (°C.) |
| 34500 | 5000 | 6.9 | 103.5 |
$^1$H-NMR (360 MHz, d$^8$-THF)
| | | |
|---|---|---|
| 2.05 ppm (s, 9H) | 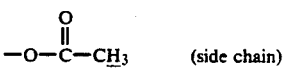 | (side chain) |
| 4.25 ppm (du, 4H) | 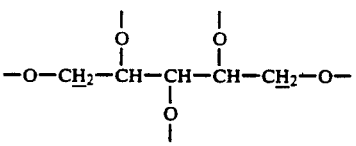 | |
| 5.45 ppm (multi, 2H) | 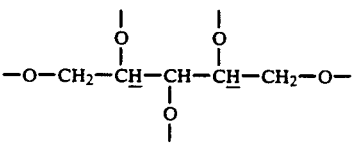 | |

5.75 ppm (tri, 1H)

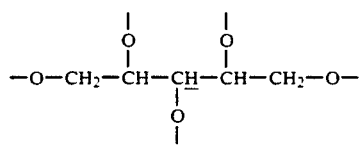

7.05 ppm (du, 4H$_a$)
8.05 ppm (du, 4H$_b$)

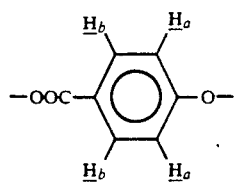

3.15 Polymerisation product of 1,8-diphenoxy-3,6-dioxytriethane-p,p'-diacetic acid with acetic anhydride

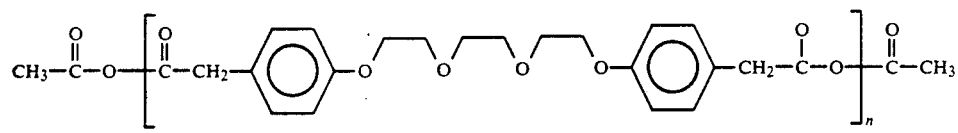

| Product No. | GPC | DSC Tg (°C.) |
|---|---|---|
| 1 | not possible | 12.8 |
| 2 | " | 18.1 |

$^1$H—NMR (360 MHz, DMSO) analogous to the $^1$H—NMR of compound 3.4, signals slight displaced merely a new signal at δ=3.45 ppm (s,4H)

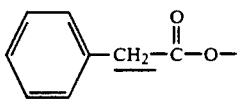

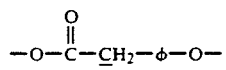

3.16 Polymerisation product of 1,3-diphenoxy-propan(2)ol-p,p'-diacetic acid with acetic anhydride

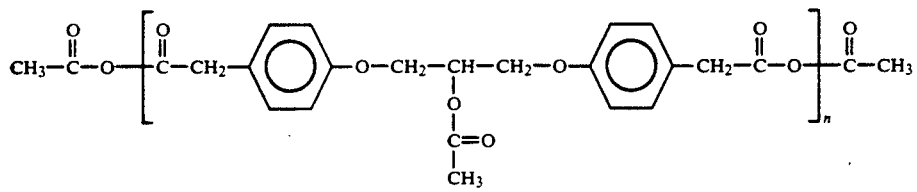

DSC: Tg=47.8° C.
$^1$H—NMR (360 MHz, DMSO) analogous to compound 3.8, signals slightly displaced, merely a new signal at δ=3.5 ppm (s,4H)

3.17 Polymerisation of 1,3-diphenoxy-propan(2)ol-p,p'-diacetic acid with butyric anhydride

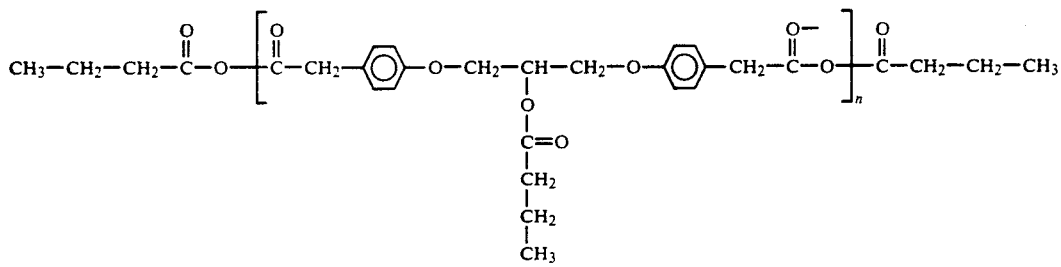

DSC: Tg=36° C.

3.18 Copolymerisation product of 1,8-diphenoxy-3,6-dioxytriethane-p,p'-dicarboxylic acid with 1,3-diphenoxy-propan(2)-ol-p,p'-dicarboxylic acid and acetic anhydride

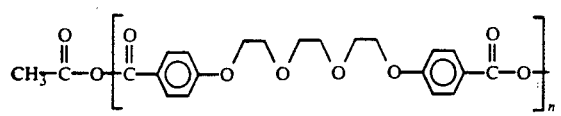

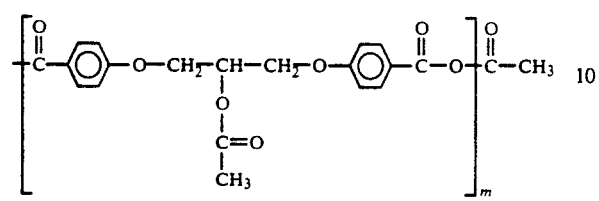

| Product No. | Molar ratio n:m | GPC (CH₂Cl₂/detection 275 nm) | | | DSC Tg/°C. |
|---|---|---|---|---|---|
| | | $M_w$ | $M_n$ | $M_w/M_n$ | |
| 1 | 9:1 | 48000 | 15000 | 3.2 | 41.0 |
| 2 | 3:1 | 30000 | 11000 | 2.7 | 43.6 |
| 3 | 3:1 | 57000 | 5500 | 10.3 | 55.2 |
| 4 | 1:1 | 24000 | 8500 | 2.8 | 55.8 |
| 5 | 1:1 | 20000 | 3500 | 5.7 | 66.8 |
| 6 | 1:3 | 17000 | 6500 | 2.6 | 63.1 |
| 7 | 1:3 | 22000 | 4500 | 4.9 | 81.0 |
| 8 | 1:3 | 58000 | 16000 | 3.6 | |
| 9 | 1:9 | 16000 | 6500 | 2.5 | 67.5 |

Product No. 4 (Synthesis is described in example 3.1):
IR(film): 1510,1580,1605 cm⁻¹ aromat; 1714,1778 cm⁻¹ anhydride; 1746 cm⁻¹ ester (intensity of the bands increases with increasing content of ester monomer element)

¹H—NMR (360 MHz, CDCl₃): The spectra represent an overlap of the homopolymer spectra with changing intensities, by means of which the composition can be determined, e.g.

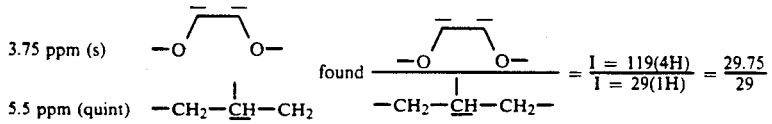

found ratio n:m = 1.02:1

3.19 Copolymerisation product of 1,8-diphenoxy-3,6-dioxytriethane-p,p'-dicarboxylic acid with 1,3-diphenoxy-propan(2)ol-m,m'-di-carboxylic acid and acetic anhydride

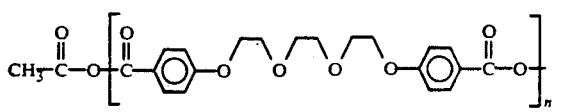

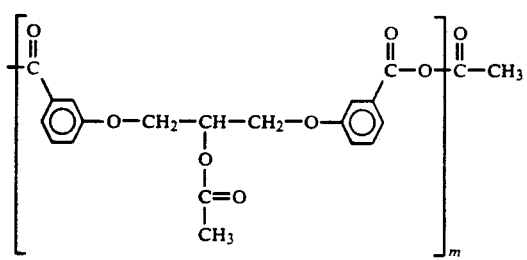

Molar

| Product No. | ratio n:m | GPC (CH₂Cl₂/detection 275 nm) | | | DSC Tg (°C.) |
|---|---|---|---|---|---|
| | | $M_w$ | $M_n$ | $M_w/M_n$ | |
| 1 | 9:1 | 55500 | 10500 | 5.3 | 43.5 |
| 2 | 3:1 | 52000 | 11500 | 4.5 | 46.6 |
| 3 | 1:1 | 50500 | 11500 | 4.4 | 50.4 |
| 4 | 1:3 | 12500 | 2500 | 5.0 | 50.5 |
| 5 | 1:9 | 16000 | 3000 | 5.3 | 57.6 |

Product No. 3.
IR(film): 1488 (meta), 1510 (para), 1583, 1605 cm⁻¹ aromatic; 1719, 1781 cm⁻¹ anhydride; 1742 cm⁻¹ ester
Intensity ratio of 1488 to 1510 cm⁻¹ varies dependent on the composition 3.20 Copolymerisation product of 1,8-diphenoxy-3,6-dioxytriethane-m,m'-dicarboxylic acid with 1,3-diphenoxy-propan(2)-ol-p,p-dicarboxylic acid and acetic anhydride

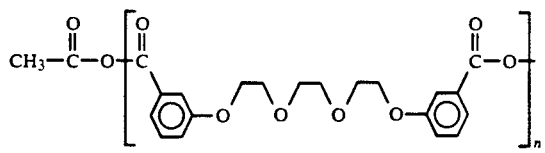

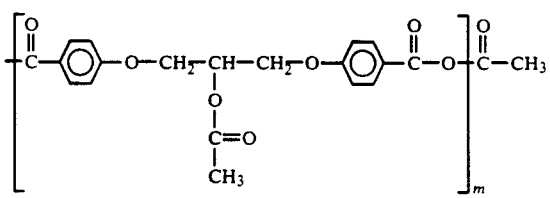

Molar

| Product No. | ratio n:m | GPC (CH₂Cl₂/detection 275 nm) | | | DSC Tg (°C.) |
|---|---|---|---|---|---|
| | | $M_w$ | $M_n$ | $M_w/M_n$ | |
| 1 | 9:1 | 9500 | 2500 | 3.8 | 23.3 |
| 2 | 3:1 | 4000 | 1000 | 4.0 | 29.7 |
| 3 | 1:1 | 26000 | 7000 | 3.7 | 45.6 |
| 4 | 1:3 | 23000 | 6500 | 3.5 | 61.1 |
| 5 | 1:9 | 16500 | 5500 | 3.0 | 68.5 |

3.21 Copolymerisation product of 1,8-diphenoxy-3,6-dioxytriethane-m,m'-dicarboxylic acid with 1,3-diphenoxy-propan(2)-ol-m,m'-dicarboxylic acid and acetic anhydride

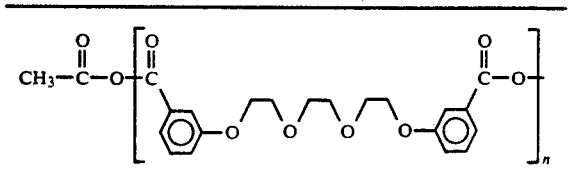

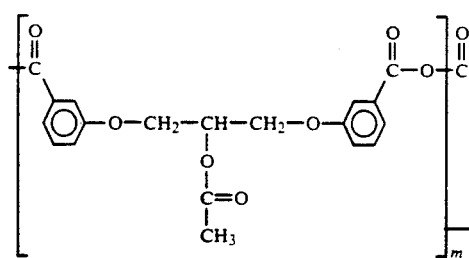

| Product No. | Molar ratio n:m | GPC (CH$_2$Cl$_2$/detection 250 nm) | | | DSC Tg (°C.) |
|---|---|---|---|---|---|
| | | M$_w$ | M$_n$ | M$_w$/M$_n$ | |
| 1 | 9:1 | 6000 | 1000 | 6.0 | 18.2 |
| 2 | 3:1 | 14500 | 2000 | 7.3 | 20.2 |
| 3 | 1:1 | 15000 | 2500 | 6.0 | 34.9 |
| 4 | 1:3 | 15000 | 2500 | 6.0 | 52.0 |

| | | | | | |
|---|---|---|---|---|---|
| 5 | 1:9 | 21000 | 4000 | 5.3 | 59.9 |

3.22 Copolymerisation product of 1,11-diphenoxy-3,6,9-trioxytetraethane-p,p'-dicarboxylic acid with 1,3-diphenoxypropan(2)ol-p,p'-dicarboxylic acid and acetic anhydride

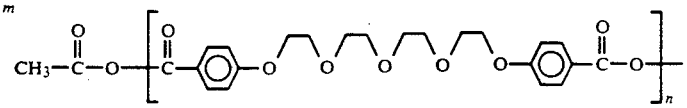

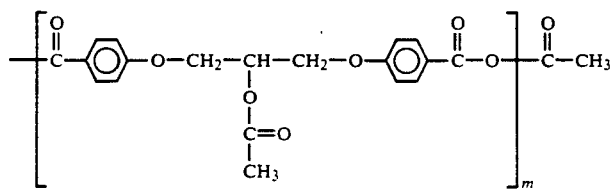

| Product No. | Molar ratio n:m | GPC (CH$_2$Cl$_2$/detection 275 nm) | | | DSC Tg (°C.) |
|---|---|---|---|---|---|
| | | M$_w$ | M$_n$ | M$_w$/M$_n$ | |
| 1 | 9:1 | 37000 | 10000 | 3.7 | 22.3 |
| 2 | 3:1 | 23000 | 6000 | 3.8 | 28.3 |
| 3 | 1:1 | 34000 | 14000 | 2.4 | 51.6 |
| 4 | 1:3 | 26000 | 9000 | 2.9 | 60.5 |
| 5 | 1:9 | 20000 | 7000 | 2.9 | 68.0 |

Product No. 3

IR(film): 1510,1581,1605 cm$^{-1}$ aromat; 1714,1777 cm$^{-1}$ anhydride; 1746 cm$^{-1}$ ester (intensity of the bands increases with increasing content of ester monomer elements)

$^1$H—NMR (360 MHz, CDCl$_3$); The spectra represent an overlap of the homopolymers with changing intensities, by means of which the composition can be determined, e.g.:

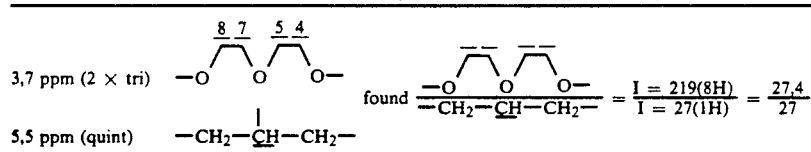

found ratio n:m = 1:1.01

3.23 Copolymerisation product of 1,11-diphenoxy-3,6,9-trioxytetraethane-p,p'-dicarboxylic acid with 1,3-diphenoxypropan(2)ol-m,m'-dicarboxylic acid and acetic anhydride

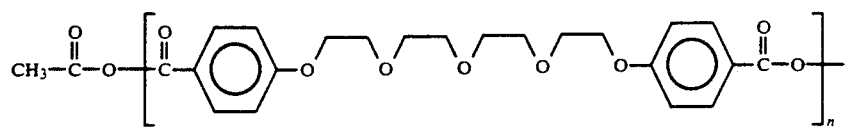

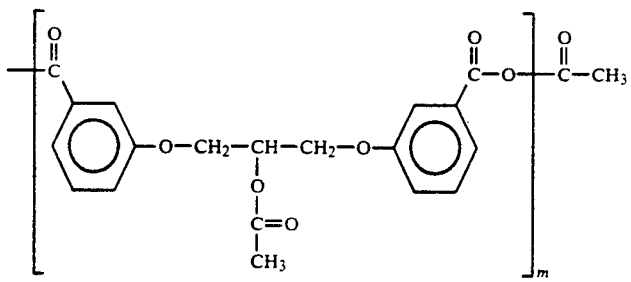

| Product No. | Molar ratio n:m | GPC(CH$_2$Cl$_2$/detection 275 nm) | | | DSC Tg (°C.) |
|---|---|---|---|---|---|
| | | M$_w$ | M$_n$ | M$_w$/M$_n$ | |
| 1 | 9:1 | 30000 | 7500 | 4.0 | 24.9 |
| 2 | 3:1 | 26000 | 6500 | 4.0 | 21.3 |
| 3 | 1:1 | 26000 | 7000 | 3.7 | 40.5 |
| 4 | 1:3 | 26000 | 7500 | 3.5 | 52.8 |
| 5 | 1:9 | 28000 | 6000 | 4.7 | 58.4 |

3.24 Copolymerisation product of 1,8-diphenoxy-3,6-dioxytriethane-p,p'-dicarboxylic acid with sebacic acid and acetic 3.25 Copolymerisation product of 1,8-diphenoxy-3,6-dioxytriethane-p,p'-dicarboxylic acid with 1,8-diphenoxy-3,6-dioxytriethane-p,p'-diacetic acid and

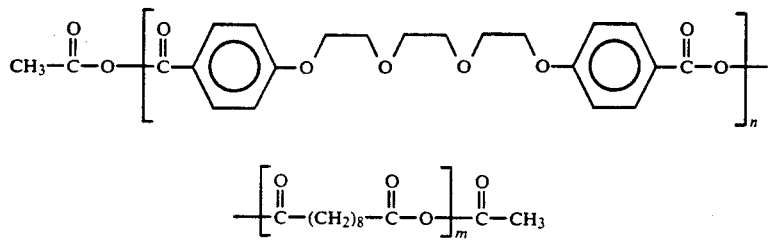

| Product No. | Molar ratio n:m | DSC Tg (°C.) | GPC |
|---|---|---|---|
| 1 | 2:1 | 18.6 | not possible |
| 2 | 9:1 | 34.6 | " |

Product 1
$^1$H-NMR (360 MHz, DMSO):

| aromatic part: | aliphatic part: |
|---|---|

3.65 ppm (s) —O⌒O—

3.8 ppm (tri) -φ-O—CH$_2$—C$\underline{H}_2$—

4.2 ppm (tri) -φ-O—C$\underline{H}_2$—CH$_2$—

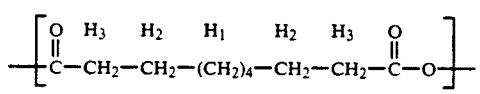

1.3 ppm (s, H$_1$)
1.55 ppm (quint), H$_2$)
2.2 ppm (tri, H$_3$)

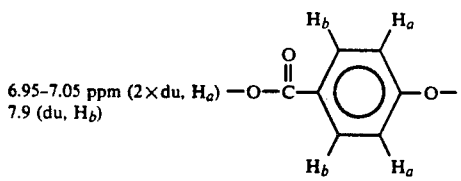

6.95-7.05 ppm (2×du, H$_a$)
7.9 (du, H$_b$)

Determination of the composition:
$$\frac{\Sigma CH_2(aliph.)}{\Sigma H(arom.)} = \frac{130\ (16H)}{144\ (8H)} \text{ found } = \frac{1}{2.2}$$

acetic anhydride

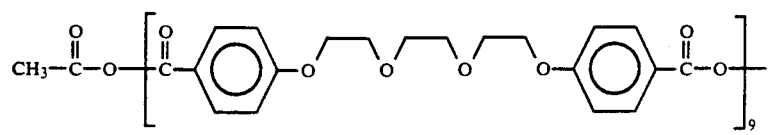

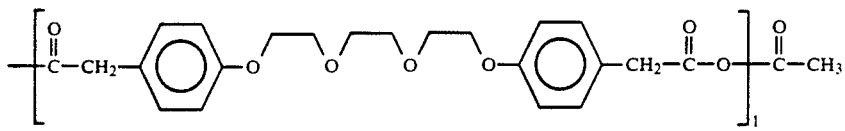

DSC: Tg=42.3° C.

The molecular weights of the compounds prepared were determined by GPC (Gelpermeationchromatography) in $CH_2Cl_2$ or THF. The elution volumina were calibrated with anionic polymerised calibration styrenes of Dupont Instruments.

The column material consisted of cross linked polystyrene defined with divinylbenzene.

The two used PLg-columns (7.5×300 mm) of Polymer Laboratories U.K. had pore diameters of 500 and $10^4$ Angstrom.

Degradability in vitro

EXAMPLE 4

The in vitro degradability of products Nos. 4, 8 and 10 of Example 3.4 was determined at 37° C. in water of a pH 7.

300 mg of these products were added to the water in fine-grained powder form, and left to slowly decompose.

After a certain time, the sample was isolated and washed with water buffered to pH 7.4, whereupon the water-soluble monomer could be removed.

Figure 3:
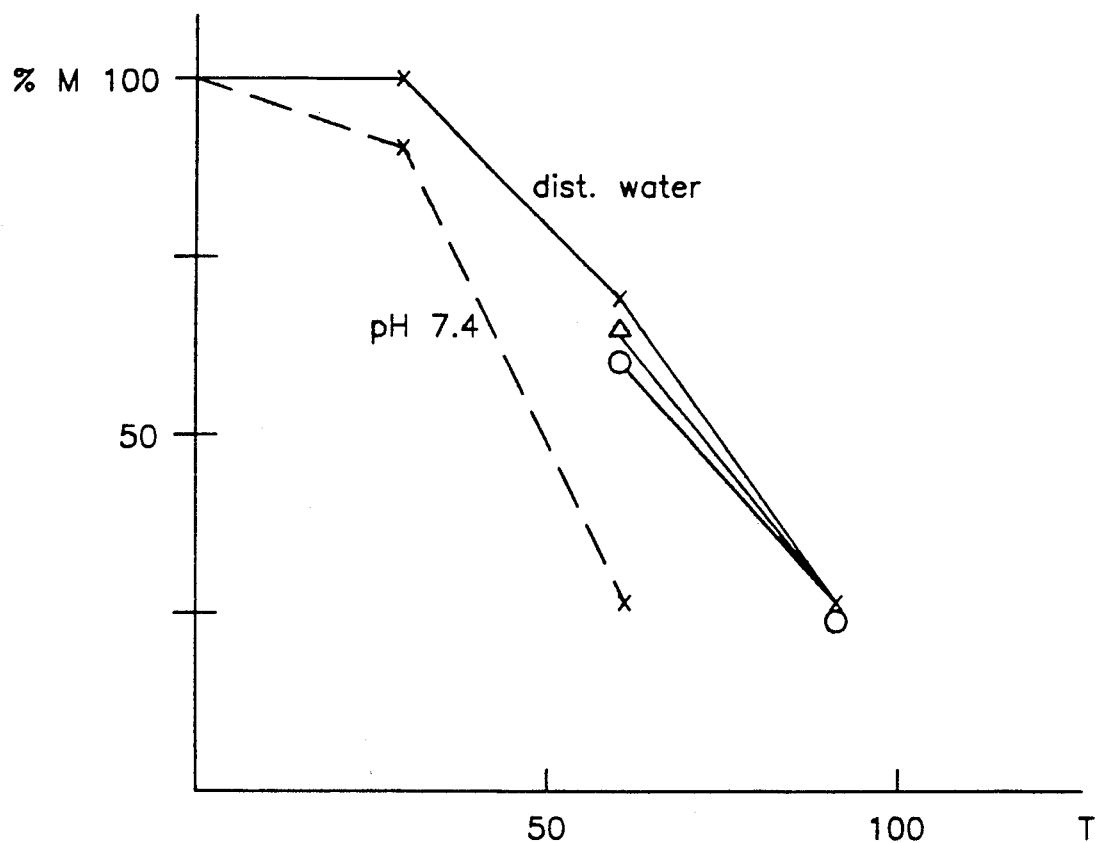

The remaining mass was dried and its weight determined by weighing. The degradation results were shown graphically in FIG. 3 (remaining mass M in percentages vs. degradation time in days).

After 90 days the remaining mass was reduced to about 25% of weight, indicating that the class of substances is hydrolytically degraded in reasonable time periods. A degradation down to 25% of remaining mass in water of pH 7.4 can be realized within about 60 days (see FIG. 3)

EXAMPLE 5

Figure 4:
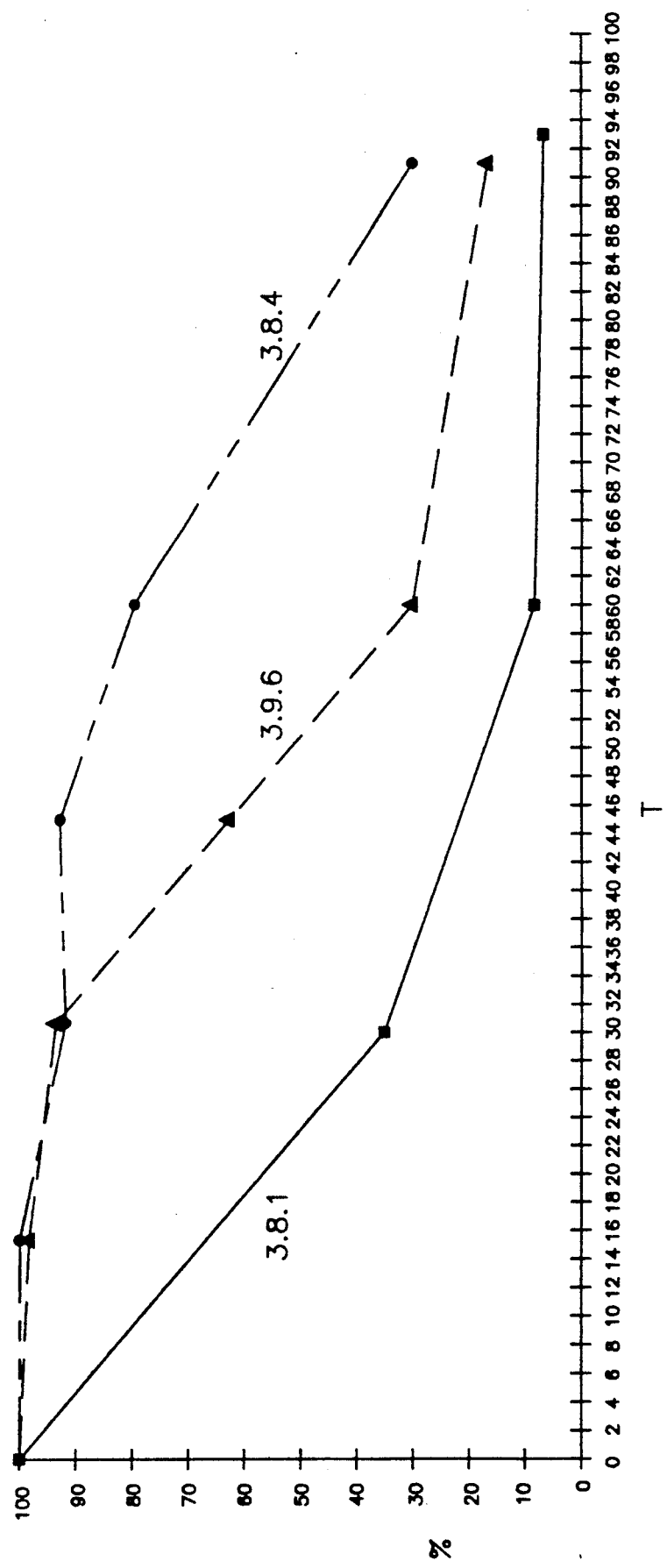
Figure 5:
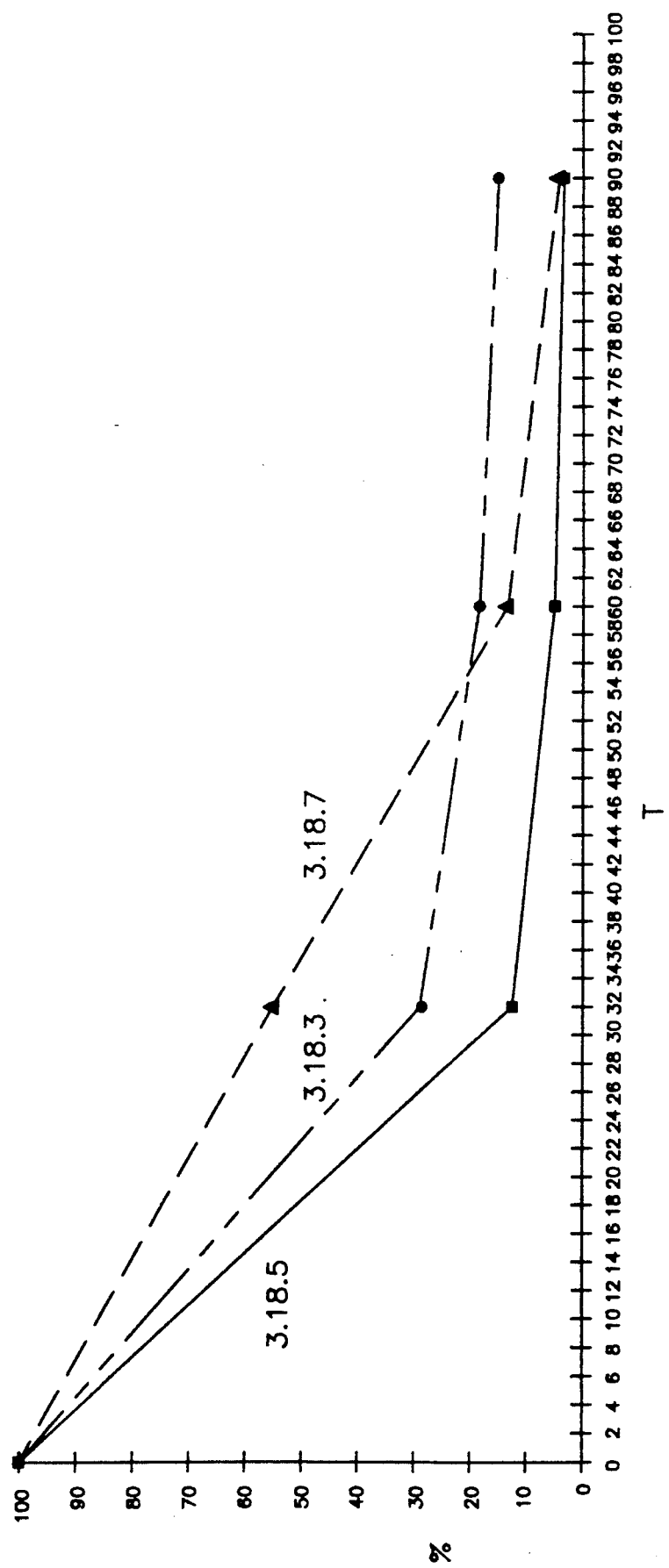

In contrast to Example 4 the in vitro degradation times were determined according to the method described in Example 4, in phosphate buffer pH 7.4 at 37° C. for the following products and were registered in the following figures:

| Product of Example | 3.8 | No 1 FIG. 4 | 3.18 | No 3 FIG. 5 |
|---|---|---|---|---|
|  |  | No 4 FIG. 4 |  | No 5 FIG. 5 |
|  | 3.9 | No 6 FIG. 4 |  | No 7 FIG. 5 |

Degradability in vivo

EXAMPLE 6

From the products of Examples 3.8 No 1 and 4, 3.9 No 6 and 3.18 No 5, 3 and 7 round pressed objects of a diameter of 5 mm (tablet form) were made and implanted i.p. in rats for different time periods.

Figure 6:
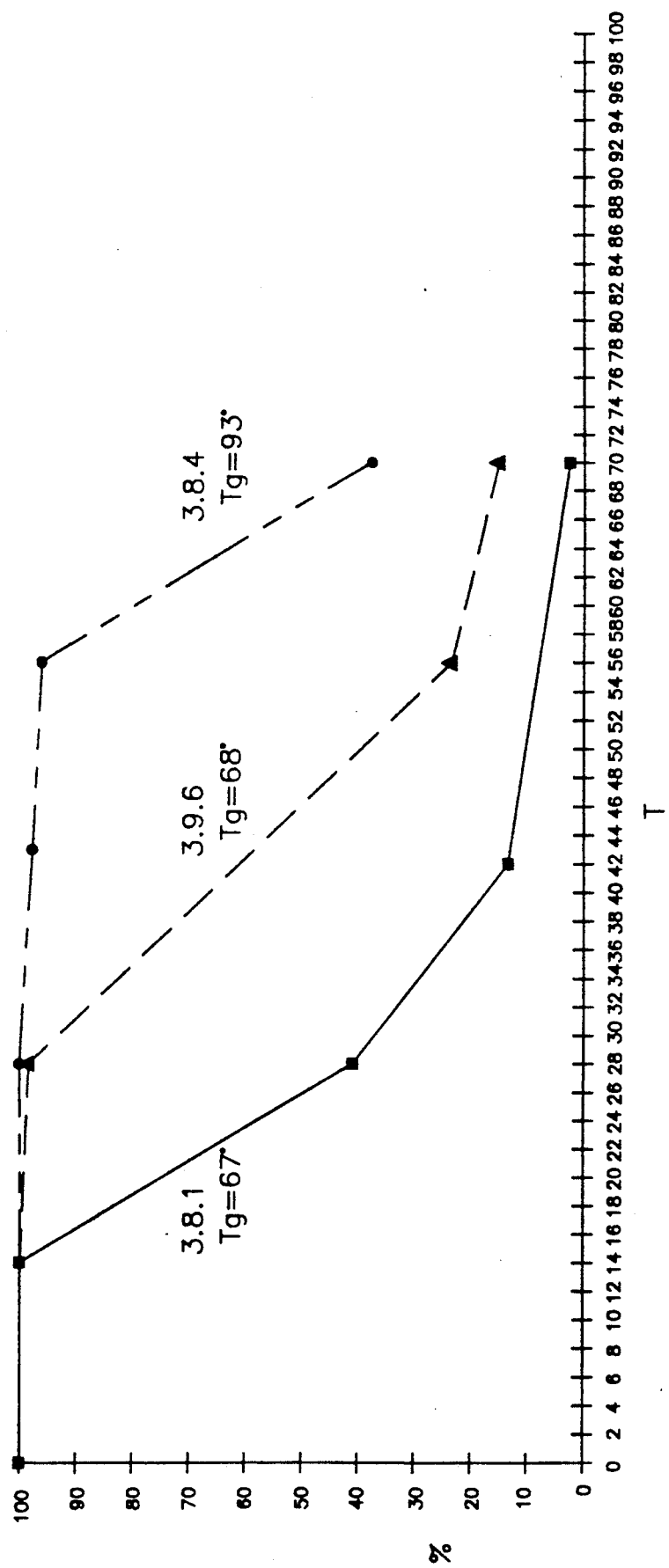
Figure 7:
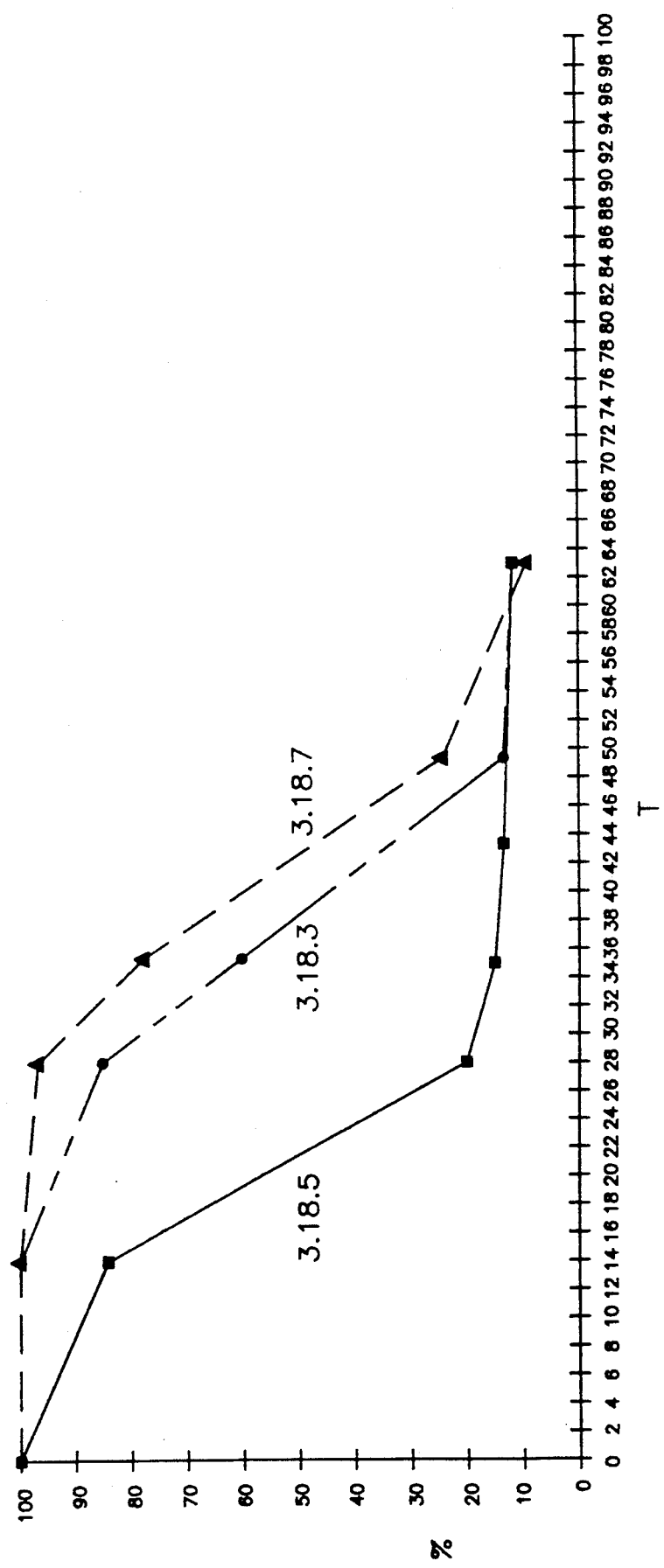

The mass loss was determined gravimetrically and are shown for the products of Examples 3.8 and 3.9 in FIG. 6 and for the products of Example 3.18 in FIG. 7 (Mass loss in % of weight vs. implantation time T in days).

It appears from FIG. 6 that an increase of the molecular weight protracts the mass degradation of the products of Examples 3.8.1 and 3.8.4 of equal structure.

an accelerating influence of the decrease of the glass temperature on the mass degradation of the products of Examples 3.8.4 and 3.9.6 which have comparable molecular weights. This is in contradiction to the fact that an increase of the side chains length should result into a more hydrophatic product and thus a slower degradation.

Further it appears from comparing FIG. 4 with FIG. 6 of the products of Examples 3.8 and 3.9 the in vitro-in vivo correlation of the hydrolytic degradation is satisfactory.

Additionally it appears from FIG. 7 that the in vivo degradation time can be controlled by varying the significances in Formula I of the co-polymers of Example 3.18.5 and 3.18.7 when the products have a comparable molecular weight (20.000).

Release of pharmacologically active substance from a poly-dicarboxyl acid anhydride matrix according to the invention

EXAMPLE 7

The product of Example 3.18.8 was processed to micro-capsules, which contained Bromocriptine.

The micro-capsules were made from a 7.5% polyanhydride solution in $CH_2Cl_2$, which, based on the weight of the polyanhydride, contained 10% of active agent. The solution was spray-dried at a temperature of 50° C. in a NIRO-spray drier, at a flow speed of 15 ml/min and at a pressure interval of 2 to 5 atm. (atü).

The obtained micro capsules contained 10% of weight of active substance.

| Time: | release of active substance: |
|---|---|
| 32 h | 10.5% |
| 48 h | 12.6% |
| 56 h | 13.0% |
| 72 h | 13.8% |

EXAMPLE 8

In analogous manner as described in Example 7 micro-capsules were produced, which contained bromocriptine as the active substance.

The parameters during spray-drying were

| temperature (entrance) | 52° C. |
|---|---|
| (exit) | 42° C. |
| pressure in the nozzle | 2,5 bar |
| flow speed | 28 ml/min |
| spray time | 32 min |

The micro-capsules were dried at 30° C. during 48 hours in vacuo. They contained 24.8% of active substance. The release was measured according to the paddle method as described in USP XXI, at 25° C., in water of pH 4.

| Time | Release of active substance:* |
|---|---|
| 1 h | 10.5% |
| 2 h | 24.8% |
| 4 h | 35.2% |
| 6 h | 39.8% |
| 24 h | 72.6% |
| 14 days | 90.0% |

*The release of active substance is based on the content of active substance in the micro capsules).

I claim:

1. A compound of formula II,

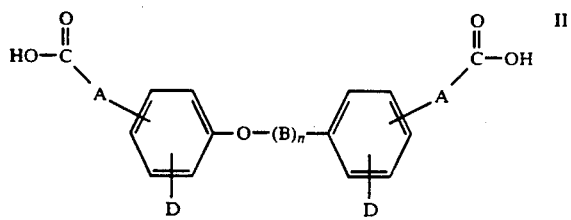

wherein

A represents a direct bond or $(C_{1-12})$ alkylene in the ortho-, meta- or para-position in the phenyl ring, and wherein B signifies $B_1 = -CH_2-CH_2-O-$ with $n>2$, $-CH_2-CH_2-CH_2-O-$ or

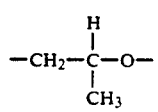

with $n>2$, or

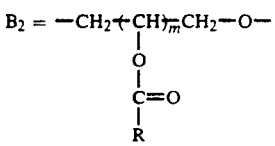

with $n=1$ and wherein $m=1,2,3$ or 4 and wherein R is $(C_{1-20})$alkyl or optionally substituted phenyl, or wherein

is a (co)(poly)ester group of one or more identical or different hydroxy carboxylic acid units, and $D = H$, $CH_3$ or $OCH_3$ in the ortho-, meta- or pha-position in the phenyl ring.

2. A compound of formula III

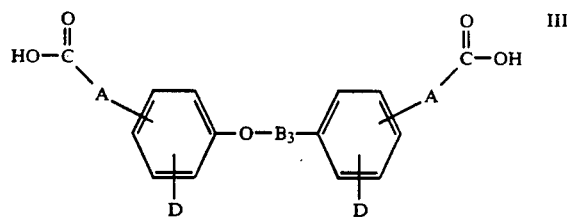

wherein

A represents a direct bond or $(C_{1-12})$alkylene in the ortho-, meta- or para-position in the phenyl ring, and wherein $D = H$, $CH_3$ or $OCH_3$ i the ortho-, meta- or para-position in the phenyl ring, and $B_3$ is

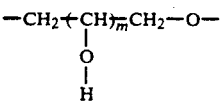

wherein $m = 1, 2, 3$ or 4.

* * * * *